United States Patent
Tan et al.

(10) Patent No.: US 12,249,067 B2
(45) Date of Patent: Mar. 11, 2025

(54) DYNAMIC MULTIMODAL SEGMENTATION SELECTION AND FUSION

(71) Applicant: GE Precision Healthcare LLC, Wauwatosa, WI (US)

(72) Inventors: Tao Tan, Nuenen (NL); Hongxiang Yi, Excelsior, MN (US); Rakesh Mullick, Bangalore (IN); Lehel Mihály Ferenczi, Dunakeszi (HU); Gopal Biligeri Avinash, Concord, CA (US); Borbála Deák-Karancsi, Budapest (HU); Balázs Péter Cziria, Budapest (HU); Laszlo Rusko, Budapest (HU)

(73) Assignee: GE Precision Healthcare LLC, Waukesha, WI (US)

( * ) Notice: Subject to any disclaimer, the term of this patent is extended or adjusted under 35 U.S.C. 154(b) by 394 days.

(21) Appl. No.: 17/664,702

(22) Filed: May 24, 2022

(65) Prior Publication Data
US 2023/0386022 A1    Nov. 30, 2023

(51) Int. Cl.
G06T 7/00     (2017.01)
A61B 8/08     (2006.01)
(Continued)

(52) U.S. Cl.
CPC .......... G06T 7/0012 (2013.01); A61B 8/0883 (2013.01); G06T 7/149 (2017.01);
(Continued)

(58) Field of Classification Search
CPC ....... G06T 7/0012; G06T 7/149; G06T 7/174; A61B 8/0883
See application file for complete search history.

(56) References Cited

U.S. PATENT DOCUMENTS

| | | | | |
|---|---|---|---|---|
| 7,864,994 B2 * | 1/2011 | Fidrich | ................. | A61B 90/36 382/128 |
| 9,336,302 B1 * | 5/2016 | Swamy | ............... | G06F 16/2465 |

(Continued)

OTHER PUBLICATIONS

International Application No. PCT/US2023/019858 filed Apr. 25, 2023—International Search Report and Written Opinion issued on Aug. 11, 2023; 14 pages.
(Continued)

*Primary Examiner* — David Bilodeau
(74) *Attorney, Agent, or Firm* — Amin, Turocy & Watson, LLP

(57) ABSTRACT

Techniques are described that facilitate dynamic multimodal segmentation selection and fusion in medical imaging. In one example embodiment, a computer processing system receives a segmentation dataset comprising a combination of different image segmentations of an anatomical object of interest respectively segmented via different segmentation models from different medical images captured of the (same) anatomical object, wherein the different medical images and the different image segmentations vary with respect to at least one of, capture modality, acquisition protocol, or acquisition parameters. The system employs a dynamic ranking protocol as opposed to a static ranking protocol to determine ranking scores for the different image segmentations that control relative contributions of the different image segmentations in association with combining the different image segmentations into a fused segmentation for the anatomical object. The system further combines the different image segmentations based on the ranking scores to generate the fused image segmentation.

25 Claims, 12 Drawing Sheets
(1 of 12 Drawing Sheet(s) Filed in Color)

(51) Int. Cl.
    *G06T 7/149* (2017.01)
    *G06T 7/174* (2017.01)
(52) U.S. Cl.
    CPC .... *G06T 7/174* (2017.01); *G06T 2207/10136* (2013.01); *G06T 2207/20061* (2013.01); *G06T 2207/20124* (2013.01); *G06T 2207/30048* (2013.01)

(56) References Cited

U.S. PATENT DOCUMENTS

| | | | |
|---|---|---|---|
| 9,968,257 B1 | 5/2018 | Burt | |
| 11,720,686 B1* | 8/2023 | Cross | G06F 21/577 726/25 |
| 2012/0230564 A1* | 9/2012 | Liu | A61B 3/0025 382/128 |
| 2021/0183070 A1* | 6/2021 | Laaksonen | G06T 7/149 |

OTHER PUBLICATIONS

Warfield et al., "Simultaneous Truth and Performance Level Estimation (STAPLE): An Algorithm for the Validation of Image Segmentation", IEEE, Transactions on Medical Imaging, vol. 23, No. 7, Jul. 2004, pp. 903-921.

Siewerdsen, J. | "Multi-Modality Imaging: Technologies, Applications, and Future Directions". Continuing Education Session MO-B-352, 50th AAPM Annual Meeting, Jul. 28, 2008, 12 pages.

Bird, D. et al | "Multimodality imaging with CT, MR and FDG-PET for radiotherapy target volume delineation in propharyngeal squamous cell carcinoma". Bird et al. BMC Cancer (2015) 15:844, DOI 10.1186/s12885-015-1867-8, 10 pages.

Wu, J. A. et al. | "Expert consensus contouring guidelines for IMRT in esophageal and gastroesophageal junction cancer". Int J Radiat Oncol Biol Phys. Jul. 15, 2015; 92(4): 911-920. doi:10.1016/j.ijrobp, 20 pages.

Salembier, C. et al. | "Estro Acrop consensus guideline on CT- and MRI-based target volume delineation for primary radiation therapy of localized prostate cancer". Radiotherapy and Oncology 127 (2018) 49-61, PMID: 29496279 DOI: 10.1016/j.radonc.2018.01.014, 13 pages.

Liu, B. et al. | "A Comprehensive Comparison of CT, MRI, Positron Emission Tomography or Positron Emission Tomography/CT, and Diffusion Weighted Imaging-MRI for Detecting the Lymph Nodes Metastases in Patients with Cervical Cancer: A Meta-Analysis Based on 67 Studies". Gynecol Obstet Invest 2017;82:209-222, DOI: 10.1159/000456006, 14 pages.

Kharuzhyk, S. et al. | "Comparison of whole-body MRI with diffusion-weighted imaging and PET/CT in lymphoma staging". European Radiology vol. 30, pp. 3915-3923 (2020), 9 pages.

Cho, S. J. et al. | "Comparison of diagnostic performance between CT and MRI for detection of cartilage invasion for primary tumor staging in patients with laryngo-hypopharyngeal cancer: a systematic review and meta-analysis". Eur Radiol. Jul. 2020;30(7):3803-3812. doi: 10.1007/s00330-020-06718-8. Epub Mar. 9, 2020, 10 pages.

Saarikko, A. et al. | "Comparison of Black Bone MRI and 3D-CT in the preoperative evaluation of patients with craniosynostosis". J Plast Reconstr Aesthet Surg. Apr. 2020;73(4):723-731. doi: 10.1016/j.bjps.2019.11.006. Epub Nov. 27, 2019, 9 pages.

* cited by examiner

DYNAMIC MULTIMODAL SEGMENTATION SELECTION AND FUSION

TECHNICAL FIELD

This application relates to medical imaging systems and more particularly to techniques for dynamic multimodal segmentation selection and fusion.

BACKGROUND

Multimodal imaging is a central component of current and future clinical and preclinical medicine. Multimodal imaging refers to the use of more than one complementary technological system that to acquire images, preferably concurrently or within a short period of time, for the purpose of diagnosis, prognostication, management and monitoring of disease. For example, various modern imaging technologies have been widely used to monitor structural, functional, and molecular changes in cancer tissues, including optical imaging (either by bioluminescence or fluorescence), computed tomography (CT), magnetic resonance imaging (MRI), positron emission tomography (PET), single-photon emission computed tomography (SPECT), ultrasound (US), MR diffusion weighted imaging (MR-DWI), and others. Each imaging modality has its own unique strengths and limitations, such as spatial/depth resolution and sensitivity. For example, MRI is considered the best imaging modality for soft tissue lesion characterization, while CT is considered better for bone metastasis analysis.

Emerging research in the field of multimodal imaging has resulted in the development of a variety of clinical opinions in literature that relate to applying contributions of different imaging modalities for evaluating specific types of anatomical objects, such as lesions and organs. These clinical opinions have been used to guide clinicians regarding how to use contributions from different imaging modalities to facilitate object/organ segmentation when available. For example, some multimodal segmentation guidelines have been developed to guide instructions regarding how to contour a particular anatomical object depending on the imaging modality (e.g., in scenarios when a single modality is available, such as CT), how to adjust the contour when additional imaging modalities of the object are available (e.g., MRI, T1, and/or T2), and how to adjust the contour when additional functional images are available (e.g., PET, SPECT, MR-DWI, etc.).

For example, in one clinical study, in addition to CT, a PET-CT was used to better contour the esophagus and the esophageal tumor. Another clinical study found that to delineate the prostate and the seminal vesicles, it beneficial to use both CT and MRI images. Another clinical study found that though MRI is the gold standard in most cases for lymph node detection, in some cases, MRI-DWI, PET or PET-CT is the most accurate and also MRI-DWI is non-irradiative. In another example, although there is no definite guideline for laryngeal cartilage infiltration (both CT and MRI are used), clinicians feel that MRI is more accurate for most patients. Based on these studies, some multimodal segmentation guidelines have been developed and defined in literature. For example, in the case of mandible (or lung) segmentation, some guidelines indicate that the contouring can be done exclusively on CT because CT displays bone and or air structures well, providing no need for adjustments based on other modalities. In another example, in the case of prostate segmentation, some guidelines indicate that the contouring can be done based on CT, but if MRI is also available the contour can be further adjusted in a more confident way (because MRI better shows the boundary of these organs). In another example, in the case of tumor segmentation, the contouring can be done based on CT, and adjusted based on MR (having better soft-tissue discrimination), and further adjusted based on PET (that highlights the active parts as well as infiltrated organs/lymph-nodes nearby), when available.

Although the literature has provided some preliminary guidelines regarding how to use contributions of different imaging modalities to facilitate segmentation of some types of anatomical objects, these guidelines are not definitive for every type of anatomical object, let alone for every combination of imaging modality. In addition, the actual contribution from each available imaging modality varies not only based on the type of the object, but for each patient and clinical site imaging system/imaging protocol. Furthermore, the contributions from different images must account for time and incremental uncertainty between the images when captured in different imaging studies, as well as differences between organ and body motion, which can vary for each patient and clinical scenario. Accordingly, techniques for automatically and intelligently accounting for all these factors to generate an optimal anatomical segmentation for a specific anatomical object and clinical context when two or more different imaging modalities are available are needed.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later. In one or more embodiments, systems, computer-implemented methods, apparatus and/or computer program products are described herein that facilitate dynamic multimodal segmentation selection and fusion.

According to an embodiment, a system is provided that comprises a memory that stores computer executable components, and a processor that executes the computer executable components stored in the memory. The computer executable components comprise a segmentation dataset comprising a combination of different image segmentations of an anatomical object of interest respectively segmented via different segmentation models from different medical images captured of the anatomical object, wherein the different medical images and the different image segmentations vary with respect to at least one of, capture modality, acquisition protocol, or acquisition parameters. The computer executable components further comprise employs a dynamic ranking protocol as opposed to a static ranking protocol to determine ranking scores (or a ranking index) for the different image segmentations that control relative contributions of the different image segmentations in association with combining the different image segmentations into a fused segmentation for the anatomical object. The computer executable components further comprise a fusion component that combines the different image segmentations based on the ranking scores to generate the fused image segmentation.

In some embodiments, elements described in connection with the disclosed systems can be embodied in different forms such as a computer-implemented method, a computer program product, or another form.

DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
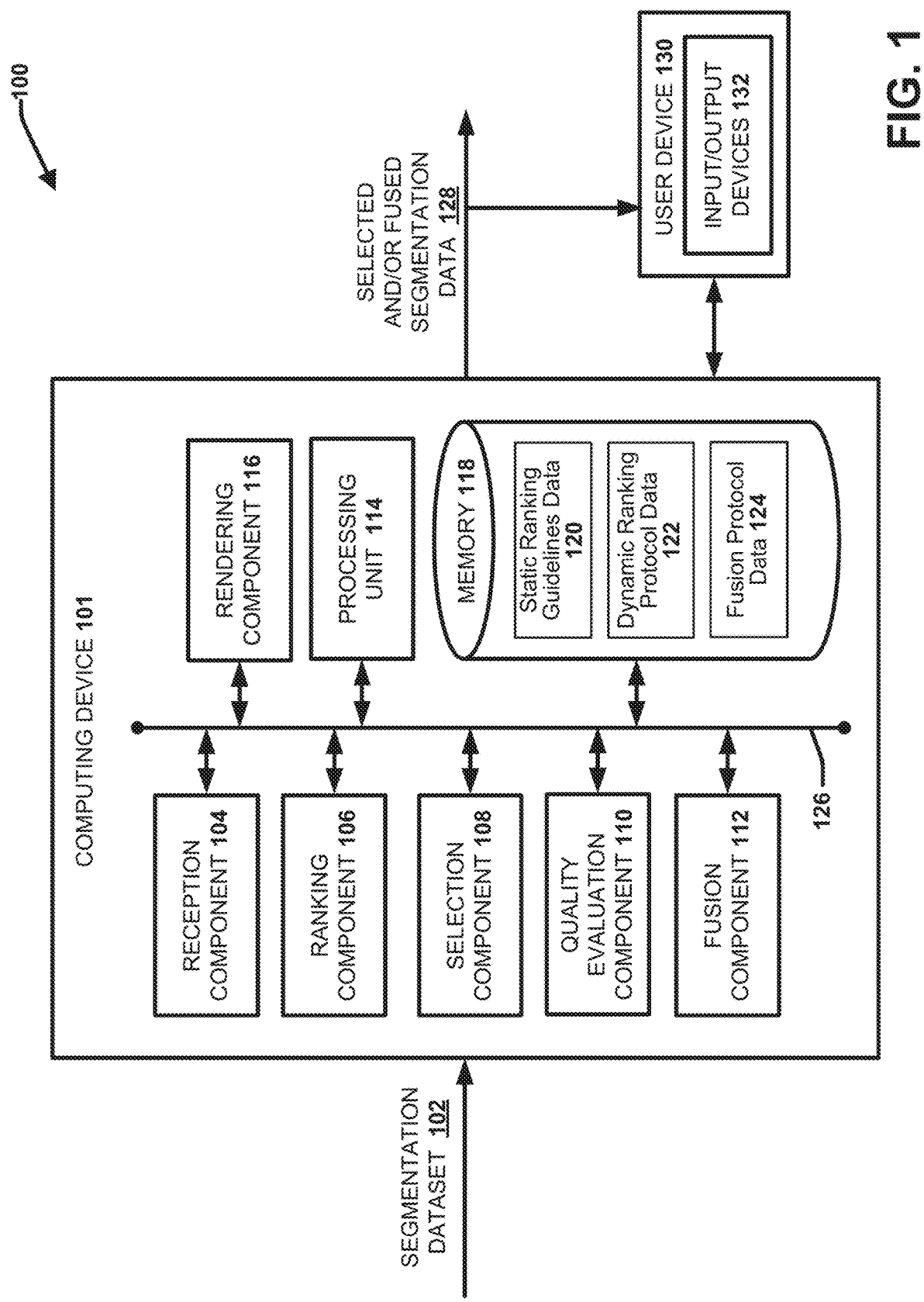
FIG. 1 illustrates an example, non-limiting system that facilitates dynamic multimodal segmentation selection and fusion in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Background section, Summary section or in the Detailed Description section.

The term "multimodal segmentation data" is used herein to refer to a segmentation dataset comprising a combination of different image segmentations of an anatomical object of interest respectively segmented via different segmentation models from different medical images captured of the anatomical object, wherein the different medical images and the different image segmentations vary with respect to at least one of, capture modality, acquisition protocol, or acquisition parameters. The disclosed subject matter is directed to systems, computer-implemented methods, apparatus and/or computer program products that facilitate filtering multimodal segmentation data in association with selecting an optimal segmentation modality for a given clinical context. The clinical context is defined at least in part based on the specific anatomical object segmented in the multimodal segmentation data and the types of imaging modalities included in the multimodal segmentation data. The subject matter is also directed to systems, computer-implemented methods, apparatus and/or computer program products that facilitate fusing multimodal segmentation data into a single synthetic image segmentation using relative contributions from each segmentation determined based in part on the given clinical usage context.

To facilitate this end, in one or more embodiments, the disclosed systems receive, access and/or optionally generate a segmentation dataset for an anatomical object. The segmentation dataset includes segmentation model generated image segmentations or segmentation masks of the anatomical object from different medical images captured and/or generated using two or more different imaging modalities (e.g., optical, CT, MRI, PET, SPECT, USI etc.), two or more different acquisition protocols, and/or two or more different acquisition parameters. Thus, each of the different segmentations or segmentations mask for the object correspond to different imaging modalities and or different images with different image properties as a result of the different acquisition protocols (e.g., contrast vs. non-contrast) and/or acquisition parameters used (e.g., automatic exposure control pattern (AEC) used, reconstruction kernel used, etc.). The segmentations or segmentation mask are generated using previously existing (i.e., previously trained) trained organ/object segmentation models.

In various embodiments, the disclosed systems employ a combination of both a static ranking protocol and a dynamic ranking protocol to rank or rate each of the different segmentations with a ranking score that reflects the relative contribution "usefulness" of the respective segmentations in association with combining the different segmentations into a single fused image segmentation for the anatomical object. In some implementations, the ranking scores determined for each segmentation are further used to control the contributions from each segmentation in association with generating a fused segmentation image for the anatomical object based on a combination of the different segmentations (e.g., a weighted fusion procedure). Additionally, or alternatively, the rankings can be used to select the "best" segmentation for clinical review and/or further processing for a given clinical usage context. As noted above, the clinical context is defined based at least in part on the specific anatomical object segmented and the types of the different imaging modalities. The clinical usage context can also be defined based on one or more additional parameters related to the intended usage of the selected or fused segmentation (e.g., radiotherapy, lesion characterization, bone metastasis analysis, diagnosis, staging, training data usage, further processing via another clinical application, etc.).

The static ranking protocol involves employing predefined segmentation guideline information determined for specific anatomical objects that defines or indicates the relative usefulness of different imaging modality segmentations for respective anatomical objects in association with combining the different imaging modality segmentations into a fused segmentation. In this regard, the predefined guideline segmentation information is based on a general understanding of the nature of how different segmentations corresponding to different imaging modalities may be combined for a given anatomical object/organ. This predefined multimodal segmentation guideline information can be determined and aggregated from available literature and clinical studies in the field, such as that described in the Background section above.

However, as noted in the Background section, although the literature may provide some preliminary guidelines regarding how to use contributions of different imaging modalities to facilitate combining different segmentations for some types of anatomical objects, these guidelines are not definitive for every type of anatomical object, let alone for every combination of imaging modality. In addition, the actual contribution from each available imaging modality varies not only based on the type of the object, but for each patient and clinical site imaging system/imaging protocol and imaging parameters used. Furthermore, the contributions from different image segmentations must account for time and incremental uncertainty between the images when captured in different imaging studies, as well as differences between organ and body motion, which can vary for each patient and clinical scenario. Even further, the disclosed techniques are applied in the context in which multimodal segmentations are provided for an anatomical object that were respectively generated via one or more existing segmentation models. In this context, the quality of the segmentations may vary from case to case depending on a variety of factors, (e.g., input image quality, presence of artifacts in the input images, model scope and accuracy capabilities, presence of anatomical variants in the input images, etc.), and thus render the static ranking protocol guidelines insufficient or inapplicable.

To account for these many contextual variabilities, the disclosed systems further provide a dynamic ranking protocol to facilitate ranking or rating the different segmentations on a case-by-case basis based on dynamic ranking factors. Unlike the static ranking protocol guidelines which provide general information for different anatomical objects regarding how different modality segmentations may be combined, the dynamic ranking factors include factors that can only be determined after imaging and organ segmentation has been completed for each patient, because the dynamic factors include those which cannot be anticipated beforehand, such as the quality of the segmentation, presence of artifacts, deviation from standard imaging protocol, etc. In this regard, in one or more embodiments, the dynamic ranking factors can include, but are not limited to: uncertainty measures associated with the different image segmentations that reflect measures of uncertainty of the one or more segmentation models with respect to the different image segmentations; quality measures for the different image segmentations that reflect one or more measures of quality of the different image segmentations; artifact information regarding presence or absence of artifacts; the acquisition protocol and acquisition parameters respectively associated with the different image segmentations; a size of the anatomical object; and a type of the anatomical object.

In some embodiments, the dynamic ranking protocol involves initially evaluating the quality of the multimodal segmentations in view of available static ranking multimodal segmentation guidelines. In this regard, if available for the specific anatomical object and clinical context, the static ranking protocol guidelines can be used to determine and apply initial ratings to each of the segmentations that reflect their relative usefulness for the clinical context. Thereafter, in accordance with the dynamic ranking protocol, the system can further tailor and adjust the rankings based a plurality of additional instance specific or "dynamic" parameters related to segmentation quality, model uncertainty, image quality, object size, object type and sub-type, imaging protocol used, image capture timing, image registration burdens, presence of bleeding, presence of artifacts, patient demography, patient pathology, and clinical usage context (among others). In some embodiments, the disclosed systems can further employ machine learning techniques to learn and define the dynamic ranking protocol guidelines based on learned patterns, correlations and/or rules between these different dynamic parameters that influence the relative ranking of available multimodal segmentations for a specific anatomical object. Additionally, or alternatively, the disclosed systems can train and develop one or more machine learning models to automatically infer the ranking scores for respective multimodal segmentations for a given anatomical object and clinical context based on the learned patterns, correlations and/or rules.

In some embodiments, one or more of the disclosed systems can generate a fused segmentation image for anatomical object based on the final rankings applied to each segmentation determined using the static ranking and dynamic ranking protocol. With these embodiments, the system can include a fusion component that projects the segmentations of the object into a same reference space in association with an image registration processes. The fusion component can further create the fused image by combining the registered images using the rankings for the contribution of each segmentation from the different modalities. In some implementations of the embodiments, the fusion component can apply a weighting scheme for the different segmentation modalities based on their respective ranking scores to generate the final fused segmentation image.

Additionally, or alternatively, the fusion component can employ one or more rule-based, statistical and/or machine learning algorithms to perform the fusion based at least in part on the relative rating/ranking scores. To this end, one or more embodiments of the disclosed systems can provide a learning-based contour selection workflow for specific anatomical objects such as lesions. The learning-based contour selection workflow can initially start with a (manual) data gathering phase at multiple sites (i.e., variability is acceptable in the data gathering phase so lone as just templates are defined to bound the and structure the process). During the learning phase, one or more machine learning techniques can be employed to learn the optimal ways to fuse different segmentation modalities available for each type of anatomical object based on the various static and dynamic parameters discussed above and evaluated fusion quality outcomes. Thereafter, the system can apply the learned optimal fusion mechanisms (e.g., in the form of learned rules and/or trained fusion models) in an inferencing phase for an automated segmentation selection and fusion workflow.

The types of medical images processed/analyzed using the techniques described herein can include images captured using various types of image capture modalities. For example, the medical images can include (but are not limited to): radiation therapy (RT) images, X-ray (XR) images, digital radiography (DX) X-ray images, X-ray angiography (XA) images, panoramic X-ray (PX) images, computerized tomography (CT) images, mammography (MG) images (including a tomosynthesis device), a magnetic resonance imaging (MRI or simply MR) images (including T1-weighted images and T2-weighted images), ultrasound (US) images, color flow doppler (CD) images, position emission tomography (PET) images, single-photon emissions computed tomography (SPECT) images, nuclear medicine (NM) images, optical, MR-DWI and the like. The medical images can also include synthetic versions of native medical images such as synthetic X-ray (SXR) images, modified or enhanced versions of native medical images, augmented versions of native medical images, and the like generated using one or more image processing techniques. The types of medical image data processed/analyzed herein can include two-dimensional (2D) image data, three-dimensional image data (3D) (e.g., volumetric representations of anatomical regions of the body), and combinations thereof.

A "modality" as used herein refers to the specific technical mode in which an image or image data is captured using one or more machines or devices. In this regard, as applied to medical imaging, different capture modalities can include but are not limited to: a 2D capture modality, a 3D capture modality, an RT capture modality, a XR capture modality, a DX capture modality, a XA capture modality, a PX capture modality a CT, a MG capture modality, a MR capture modality, an MR-T1 capture modality, an MR-T2 capture modality, a US capture modality, a CD capture modality, a PET capture modality, a SPECT capture modality, a NM capture modality, a MR-DWI modality and the like.

The term "multimodal" as applied to medical image data (including segmentation data) is used herein to refer to two or more different types of medical image data. The differentiation factor between the two or more different types of data can vary. For instance, the differentiation factor can refer to the format of the data, the capture modality of the data, the source of the data, the imaging protocol used, the imaging parameters used, and so one. For example, different medical images for the same anatomical object/organ corresponding to different modalities, imaging parameters and/ or imaging protocols can include (but are not limited to), an MR-T1 and an MR T2 of the object, and images of the object with without contrast agent. In another example, two different medical images corresponding to different modalities can include a diagnostic CT image captured of the object and a radiotherapy planning CT image of the object The terms "algorithm" and "model" are used herein interchangeably unless context warrants particular distinction amongst the terms. The terms "artificial intelligence (AI) model" and "machine learning (ML) model" are used herein interchangeably unless context warrants particular distinction amongst the terms.

As used in this disclosure, the term "user," and the like refers to a person, entity, system, or combination thereof that interfaces with the subject medical image processing systems using a suitable computing device.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Turning now to the drawings, FIG. 1 illustrates a block diagram of an example, non-limiting system 100 that facilitates dynamic multimodal segmentation selection and fusion in accordance with one or more embodiments of the disclosed subject matter. Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

For example, system 100 includes a computing device 101 that include several computer executable components, including reception component 104, ranking component 106, selection component 108, quality evaluation component 110, fusion component 112, and rendering component 116. These computer/machine executable components (and other described herein) can be stored in memory associated with the one or more machines. The memory can further be operatively coupled to at least one processor, such that the components can be executed by the at least one processor to perform the operations described. For example, in some embodiments, these computer/machine executable components can be stored in memory 118 of the computing device 101 which can be coupled to processing unit 114 for execution thereof. Examples of said and memory and processor as well as other suitable computer or computing-based elements, can be found with reference to FIG. 11, and can be used in connection with implementing one or more of the systems or components shown and described in connection with FIG. 1 or other figures disclosed herein.

The memory 118 can further store a variety of information that is received by, used by, and/or generated by the computing device 101 in association with that facilitating dynamic multimodal segmentation selection and fusion. In the embodiment, shown, this information includes (but is not limited to), static ranking guidelines data 120, dynamic ranking protocol data 122 and fusion protocol data 124. In various embodiments, system 100 is configured to receive segmentation dataset 102 (e.g., via reception component 104) and process the segmentation dataset 102 to generate selected and/or fused segmentation data 128. The segmentation dataset 102 can include a combination of different image segmentations of an anatomical object of interest respectively segmented via different segmentation models from different medical images captured of the anatomical object, wherein the different medical images and the different image segmentations vary with respect to at least one of, capture modality, acquisition protocol, or acquisition parameters. The selected and/or fused segmentation data 128 can comprise a selected subset (e.g., one or more) of the segmentation dataset 102 and/or fused segmentation image generated by the computing device 101 (e.g., using fusion component 112) by intelligently combining or fusing the different image segmentations in a manner that results in a single segmentation for the anatomical object that optimizes contributions from the different segmentation modalities.

Any information received (e.g., segmentation dataset 102) and/or generated (e.g., selected and/or fused segmentation data 128) by the computing device 101 can be presented or rendered to a user via a suitable display. In the embodiment shown, this display can be associated with a user device 130 (i.e., the input/output devices 132 can include a display) that can be communicatively and operatively coupled (e.g., vie one or more wired or wireless communication connections) to the computing device 101. In this regard, the user device 130 can correspond to a computing device employed by a user (e.g., a clinician, a radiologist, a technician, a machine learning (ML) model developer, or the like) to interface with one or more features and functionalities provided by the respective components of the computing device 101. For example, in various embodiments, one or more of the components of the computing device 101 can be associated with a medical imaging application that facilitates accessing and reviewing medical images via an interactive graphical user interface (GUI) displayed at the user device 130, generating and reviewing anatomical object segmentations for the medical images via the GUI, annotating the medical images, running inferencing models on the medical images and the like. In some implementations of these embodiments, the computing device 101 can correspond to an application server that provides at least some of these features and functionalities to the user device 130 via a network accessible platform, such as a web-application or the like. With these embodiments, the user device 130 can be communicatively coupled to the computing device 101 via one or more wired or wireless communication networks (e.g., the Internet) and access one or more of the features and functionalities of the computing device 101 as a web-application using a suitable web browser. Additionally, or alternatively, system 100 can employ a local deployment architecture wherein one or more components of the computing device 101 are deployed locally at the user device 130. Various other deployment architectures for system 100 and other systems describe herein are envisioned. The user device 130 can include one or more input/output devices 132 (e.g., a keyboard, a mouse, a touchscreen, a display, etc.) that provide for receiving user input in association with usage of the feature and functionalities of the computing device 101 and displaying an associated GUI. Examples of some suitable input/output devices 132 are described with reference to FIG. 11 with respect to input devices 1128 and output device 1136).

In accordance with system 100, the reception component 104 can receive the segmentation dataset 102 for processing by the computing device 101. As noted above, the segmentation dataset 102 includes anatomical object segmentation data for the same anatomical object as depicted in two or more different medical images captured and/or generated from the same subject using different medical imaging modalities (e.g., optical, CT, MRI, PET, SPECT, US, etc.). The number and type of different medical images and corresponding imaging modalities can vary. The anatomical object segmentation data can include information that defines the boundary or contour of the anatomical object in 2D and/3D (depending on the type of image from which its segmented) relative to the original image data from which it was segmented. For example, the segmentation data can correspond to a segmentation mask applied to the anatomical object, image mark-up data including boundary lines, points, circles, etc. of the anatomical object, and/or image data of the anatomical object as extracted from the input image. The segmentation dataset 102 can further include the original medical image data from which the corresponding segmentations were generated. In some embodiments, the segmentation dataset 102 can include segmentations data for a single anatomical object of interest depicted in the respective multimodal images. In other embodiments, the segmentation dataset 102 can include segmentations data for a plurality of different anatomical object of interest depicted in the respective multimodal images (e.g., generated using multiorgan segmentation models).

Figure 2:
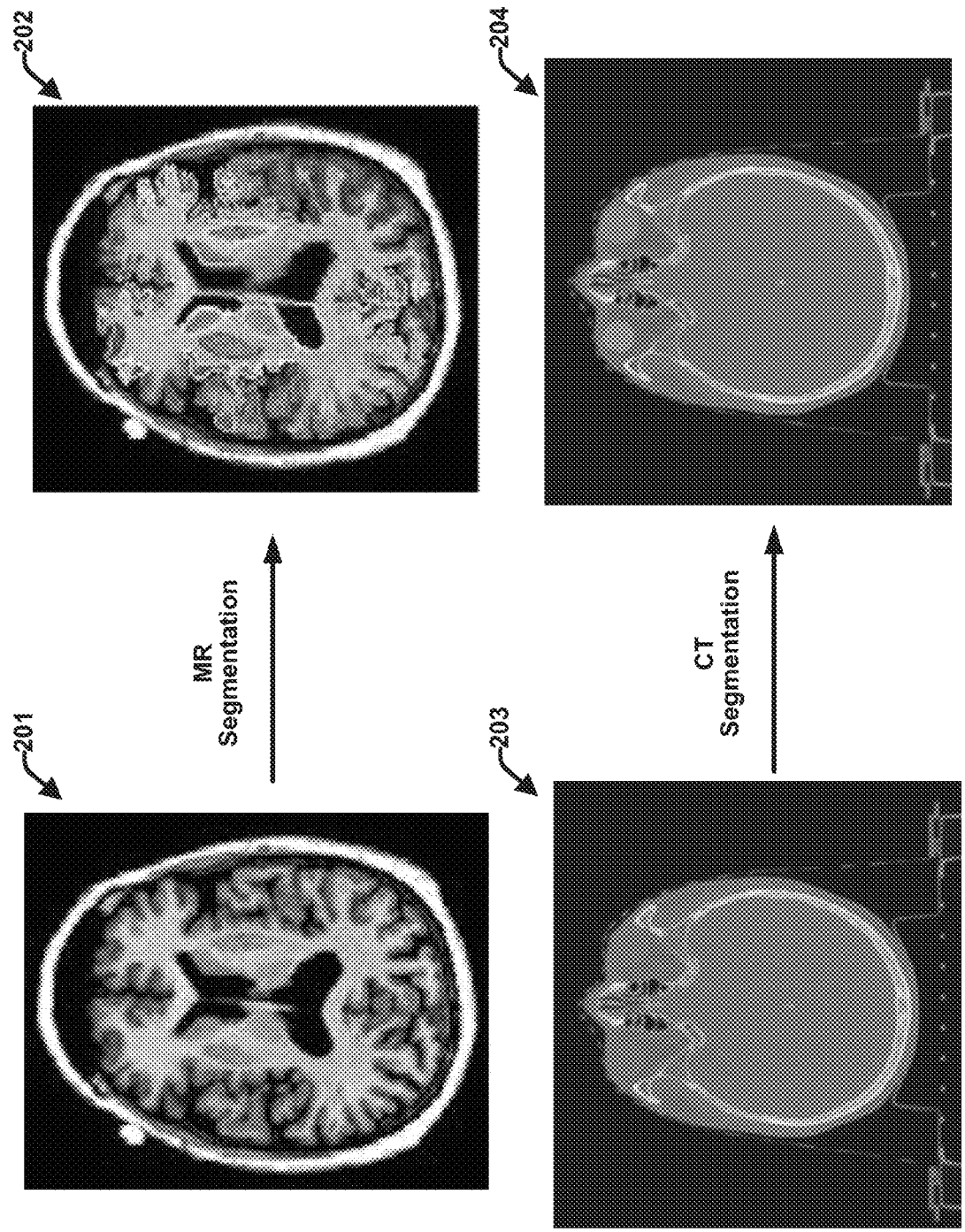
FIG. 2 presents example multimodal segmentation data in accordance with one or more embodiments of the disclosed subject matter.

FIG. 2 presents example multimodal segmentation data in accordance with one or more embodiments of the disclosed subject matter. In the example shown in FIG. 2 the multimodal segmentation data includes MR segmentation data 201 generated from MR image data 201 corresponding to an MR brain scan of a patient. The multimodal segmentation data further includes CT segmentation data 204 generated from CT image data 203 corresponding to a CT brain scan of the same patient. The MR segmentation data 202 provides segmentation data in the form of segmentation boundary marks or contours around various defined anatomical objects (e.g., tissues, vessels, regions of interest (ROIs), etc.) depicted in the MR image data 201. The CT segmentation data 204 provides segmentation data in the form of a segmentation mask over the entirety of the brain as depicted in the CT image data 203. It should be appreciated that the multimodal segmentation data depicted in FIG. 2 is merely exemplary and a variety of different types of segmentation data for a variety of different anatomical objects associated with all regions of the body are envisioned.

With reference again to FIG. 1, in accordance with the disclosed techniques, the segmentation dataset 102 corresponds to anatomical object image segmentations (e.g., such as those depicted in FIG. 2) as segmented from the respective original 2D and/or 3D medical images using one or more existing segmentation models. For example, in some implementations, the segmentation models can include separate segmentation models tailored to different anatomical objects and/or different imaging modalities. In other implementations, one or more of the segmentation models may be configured to process input images from different imaging modalities to generate the corresponding segmentations. Additionally, or alternatively, the segmentation models can include multi-organ/multi-object segmentation models configured to generated segmentation data for a set of defined anatomical objects depicted in the input image data.

In various embodiments, each of the image anatomical object segmentations (i.e., the segmentation model outputs) included the segmentation dataset 102 can further include one or more uncertainty measures that reflect estimated measures of certainty or uncertainty associated with the respective segmentation models that generated the corresponding segmentation data. In this regard, the one or more uncertainty measures reflect a measure of certainty associated with segmentation model's confidence in the accuracy and/or specificity of the segmentation data generated thereby. Typically, the segmentation models can be configured to output this uncertainty measure data in addition to the corresponding segmentation data. The type of the uncertainty measure data can vary. For example, the uncertainty measure data can include but is not limited to, a certainty estimate score, a confidence score, a confidence interval, an accuracy score, a DICE score, or the like.

The segmentation dataset 102 can further include a variety of rich metadata associated with each of the anatomical object segmentations and/or the original image data from which they were generated. For example, the metadata associated with each original input image data and associated anatomical object segmentation can include information identifying the type of imaging modality, the imaging protocols and parameters used to generate the original image data, the make/model of the imaging system used to capture the original image data, timestamp information describing the timing of capture of imaging data, and information identifying the source or site of the original medical image data (e.g., cite name/location). The metadata can also include information describing image feature properties associated with the original image data from which the segmentations were generated, such as information regarding image resolution, brightness, pixel spacing and grid size, acquisition plane/angle, noise levels, and the like. Each of the segmentations can also be associated with metadata that defines or indicates the specific anatomical object name or classification in accordance with a defined clinical ontology (e.g., the specific organ, lesion, lesion type, tumor, vesicle, bone, soft tissue, etc.). In some implementations, each of the segmentations can also be associated with metadata that defines or indicates geometrical properties of the segmentation, such as but not limited to, the relative size, position and geometry of the anatomical object (e.g., organ/lesion diameter), information defining the segmentation boundary or contour, and the like.

In some embodiments, the metadata can also include information identifying or indicating the quality of the respective anatomical object segmentations (i.e., segmentation quality information). For example, the segmentation quality information can include one or more quality measures that reflect the degree to which the segmentation contour correctly and clearly defines the boundary of the anatomical object relative to the original image data from which it was segmented. The quality information can also include a connectivity measure that represents a degree of connectivity in of the contour or boundary line around the segmented anatomical object. The quality information can also include information identifying or indicating whether any artifacts are depicted in the original image data and/or the segmentation data (which typically degrades the image and corresponding segmentation quality). The quality information can also include one or more noise measures that represent levels of noise in the image segmentations. Additionally, or alternatively, information regarding the segmentation quality for each segmentation can be determined by the quality evaluation component 110 and/or received as user feedback in association with presentation of the segmentation dataset 102 to one or more users (e.g., via the user device 130). the contrast measures, segmentation contour connectivity measures, etc.).

The segmentation dataset 102 an also include information regarding the patient or subject represented in the segmentation dataset 102. For example, the patient information can include demographic information for the patient, such as but not limited to, age, gender, ethnicity, location, body mass index (BMI), height and weight. The patient information can also include relevant pathology information for the patient extracted from radiology reports associated with the original medical images, and/or the patients medical records. The patient information can also include other relevant medical history information for the patient, such as information regarding comorbidities, past diagnosis information, and the like.

The ranking component 106 can be configured to rank or rate the respective segmentations included in the multimodal data 102 with a ranking score that reflects the relative usefulness of the respective segmentations for a given clinical context. In one or more embodiments, to facilitate this end, the ranking component 106 can employ a static ranking protocol, a dynamic ranking protocol, or a combination thereof. The scale used for the ranking score can vary. For example, in some implementations, the ranking scores can merely reflect a ranking order of the respective segmentations (e.g., first=highest ranked, second=second highest ranked, third=third highest ranked, and so on). In another example, the ranking scores can reflect relative weighted contributions of the respective segmentation as a percentage contribution. Other ranking score scales are envisioned.

In some implementations, the ranking scores determined for each segmentation can be used by the fusion component 112 to control the contributions from each segmentation in association with generating a fused segmentation image for the anatomical object based on a combination of the different segmentations (e.g., weighted fusion). Additionally, or alternatively, the rankings can be used by the selection component 108 to select the "best" segmentation for clinical review and/or further processing for a given clinical usage context. As noted above, the clinical context is defined based at least in part on the specific anatomical object segmented and the distribution of the different types of corresponding imaging modalities. The clinical context can also be defined based on one or more additional parameters related to the intended usage of the selected or fused segmentation (e.g., radiotherapy, lesion characterization, bone metastasis analysis, diagnosis, staging, training data usage, further processing via another clinical application, etc.). With these embodiments, information defining the intended usage of the selected of fused segmentation can be included in the segmentation dataset 102, received as user feedback, and/or inferred.

The static ranking protocol involves employing predefined multimodal segmentation guideline information determined for specific anatomical objects that defines or indicates the relative usefulness of different imaging modality segmentations for respective anatomical objects and clinical contexts. This predefined multimodal segmentation guideline information can be determined and aggregated from available literature and clinical studies in the field, such as that described in the Background section above. In the embodiment shown, this predefined multimodal segmentation guideline information is represented as static ranking guidelines data 120. The static ranking guidelines data 120 can define ranking rules for ranking different combinations of image segmentation modalities for specific anatomical objects. For example, in some embodiments, the static ranking guidelines data 120 can include an indexed data structure that identifies a variety of known anatomical objects of interest that may be included in the segmentation dataset 102, such as organs, lesions, bones, tissues, vesicles, etc. according to a defined clinical ontology. For each anatomical object, the static ranking guidelines data 120 can further define different combinations of two or more types of potential types of imaging modalities in which the respective segmentations of the anatomical objects may be received. For each imaging modality combination, the static ranking guidelines data 120 can further define the relative ranking or rating score for each imaging modality included in the combination. For example, assume anatomical object A and an imaging modality combination of modality 1, modality 2, and modality 3. The relative ranking scores for this anatomical object A and imaging modality combination can indicate modality 2 is ranked highest, modality 1 is ranked second highest and modality 3 is ranked third highest. In another example, the relative ranking scores can assign a ranking percentage weight to the respective imaging modalities included in the combination, such as modality 2 is weighted 50%, modality 1 is weighted 30% and modality 3 is weighted 20%. Other ranking score scales are envisioned. In another implementation, the static or dynamic ranking protocol can also exclusively assign a "best modality" image segmentation for usage for a particular organ or anatomical object.

The level of granularity of the static ranking guidelines data 120 however is limited based on the available literature in the field and thus unlikely to provide comprehensive and conclusive ranking rules for every type of anatomical object, let alone for every combination of imaging modality segmentation and clinical usage context (e.g., radiotherapy, lesion characterization, bone metastasis analysis, diagnosis, staging, training data usage, further processing via another clinical application, etc.). In addition, the actual contribution from each available imaging modality varies not only based on the type of the object, but for each patient and clinical site imaging system/imaging protocol. Furthermore, the contributions from different images must account for time and incremental uncertainty between the images when captured in different imaging studies, as well as differences between organ and body motion, which can vary for each patient and clinical scenario. Even further, the disclosed techniques are applied in the context in which multimodal segmentations are provided for an anatomical object that were respectively generated via one or more existing segmentation models. In this context, the quality of the segmentations may vary from case to case depending on a variety of factors, (e.g., input image quality, presence of artifacts in the input images, model scope and accuracy capabilities, presence of anatomical variants in the input images, etc.), and thus render the static ranking protocol guidelines insufficient or inapplicable in many scenarios.

To account for these many contextual variabilities and inherent deficiencies in the static ranking guidelines data 120, the ranking component 106 can additionally or alternatively employ a dynamic ranking protocol to rank or rate the different multimodal segmentations for each anatomical object represented in the segmentation dataset 102 on a case-by-case basis. The dynamic ranking protocol differs from the static ranking protocol with respect to consideration and analysis of how the actual quality and visual properties of the different model generated multimodal segmentations received in the segmentation dataset 102 for a given anatomical object and subject/patient influence their relative usefulness for a given clinical context and/or for weighted fusion processing. The dynamic ranking protocol can also tailor the ranking scores for each segmented object and modality combination as a function of different candidate clinical usage contexts (e.g., radiotherapy, lesion characterization, bone metastasis analysis, diagnosis, staging, training data usage, further processing via another clinical application, etc.). The dynamic ranking protocol can further account for a variety of additional contextual variables noted above (e.g., aside from merely the anatomical object type and combination of modalities). For example, in accordance with the dynamic ranking protocol, the ranking component 106 can determine relative ranking or rating scores for the respective multimodal segmentations received for a specific anatomical object based on a variety of "dynamic" parameters related to segmentation quality, model uncertainty, image quality, clinical usage context, object size, object type and sub-type, imaging protocol/parameters used, imaging data source/site, image feature properties, image capture timing, image registration burdens (e.g., measure of geometrical alignment differences between the respective original images and/or the anatomical objects in the reference space), presence of bleeding, presence of artifacts, patient demography, patient pathology, and various other parameters that may be included in metadata associated with the respective multimodal segmentations described above (among others).

For example, in one or more embodiments, in accordance with the dynamic ranking protocol data 122, the ranking component 106 can determine rankings scores for respective multimodal segmentations received for an anatomical object based on at least the following parameters: 1.) the uncertainty measures associated with each of the segmentations (e.g., generated by the corresponding segmentation models and included in the multimodal segmentation data); 2.) one or more segmentation quality measures associated with each of the segmentations (e.g., included in the segmentation dataset 102, determined by the quality evaluation component 110 and/or received via user feedback); and 3.) anatomical object size and/or geometry in the respective segmentation (e.g., included in the segmentation dataset 102, determined by the quality evaluation component 110 and/or received via user feedback). In accordance with this example, higher measures of certainty (or lower measures of uncertainty) can correlate to a higher ranking score. Similarity, higher measures of segmentation quality (e.g., strong contour connectivity measures, high contour boundary visibility measures, low noise measure, etc. can correlate to a higher ranking score. The manner in which size measures influence the ranking score can vary based on the type of anatomical object. For example, in some implementations, for lesions, the dynamic ranking protocol can direct the ranking component 106 to increase the ranking score as function of the lesion size.

It should be appreciated that the dynamic ranking protocol data 122 is not limited to ranking the respective segmentations based on solely on the parameters in the example above. In this regard, the dynamic ranking protocol data 122 can define a plurality of complex rules between different dynamic parameters for different anatomical objects and imaging modalities that can be used by the ranking component 106 to determine relative ranking scores for each segmentation included amount a group of different multimodal segmentations. These complex rules can be based not only on evaluation of individual parameters associated with each segmentation, but relative relationships of the respective parameters between the different segmentations, such as relative timing of capture, relative size, relative quality measurements, relative model certainty measurements, and so on, that can also vary based on the type of each imaging modality, the combination of the imaging modalities, the type of the anatomical object, patent demographics, and clinical usage context.

In some embodiments, the dynamic ranking protocol can include a rule-based protocol that accounts for these various dynamic parameters to determine the relative ranking scores for each anatomical object and segmentation modality combination received in the segmentation dataset 102. Additionally, or alternatively, as described in greater detail infra, the dynamic ranking protocol can incorporate principles of artificial intelligence (AI) and machine learning (ML) to learn, define and adapt the dynamic ranking protocol over time. Information defining and/or controlling the dynamic ranking protocol is represented in system 100 as dynamic ranking protocol data 122.

In some embodiments, the dynamic ranking protocol (e.g., as defined by the dynamic ranking protocol data 122) can involves initially evaluating the quality of the multimodal segmentations in view of available static ranking guidelines data 120. In this regard, if available for the specific anatomical object, combination of multimodal image segmentations, the ranking component 106 can employ the static ranking guidelines data 120 to determine and apply initial ratings to each of the segmentations that reflect their relative usefulness for the clinical context. Thereafter, in accordance with the dynamic ranking protocol, the ranking component 106 may further tailor and adjust the relative rankings based a plurality of additional instance specific or "dynamic" parameters related to segmentation quality, model uncertainty, image quality, object size, object type and sub-type, imaging protocol used, image capture timing, image registration burdens, presence of bleeding, presence of artifacts, patient demography, patient pathology, and clinical usage context (among others).

As noted above, the dynamic ranking protocol can be based at least in part on the quality of the respective anatomical object segmentations. The quality of each segmentation can be a function of the original image quality from which the respective segmentations were generated, as well as the quality of the segmentations themselves (i.e., the outputs of the segmentation models). For example, the quality measures related to the original image quality can include one or more noise measures, one or more contrast measures, one or more brightness measures, and/or one or more general quality measures that relate to the overall quality of the respective original images. Information identifying or indicating the quality of the respective anatomical object segmentations (i.e., segmentation quality information) can include one or more quality measures that reflect the degree to which the segmentation contour correctly and clearly defines the boundary of the anatomical object relative to the original image data from which it was segmented. The quality information can also include a connectivity measure that represents a degree of connectivity in of the contour or boundary line around the segmented anatomical object. The quality information can also include information identifying or indicating whether any artifacts are depicted in the original image data and/or the segmentation data (which typically degrades the image and corresponding segmentation quality), as well as well as whether bleeding is detected in the original images.

In some implementations, (as noted above) some or all of this quality information that is used by the ranking component 106 to facilitate ranking the respective segmentations may be received with the segmentations as metadata. Additionally, or alternatively, the quality evaluation component 110 can determine one or more quality measures for the respective segmentations based on the metadata associated therewith and/or analysis of the respective segmentations using one or more image quality processing tools. For example, in some implementations, the quality evaluation component 110 can aggregate the quality information included in metadata associated with the respective segmentations to generate overall quality scores for the respective segmentations that account for the different quality measures (e.g., noise levels, contrast levels, brightness levels, segmentation contour accuracy, contour connectivity, presence of artifacts, presence of bleeding, etc.). Additionally, or alternatively, the quality evaluation component 110 can process the respective segmentation using existing image quality analysis software to determine one or more of the quality measures.

In other embodiments, one or more of these quality measures can be received as user feedback in association with presentation of the respective multimodal segmentations to one or more users by the rendering component 116. With these embodiments, prior to determining the rankings of the respective segmentations, the rendering component 116 can present the received multimodal segmentations to one or more users (e.g., via their respective user devices 130) via an interactive GUI that includes a mechanism for providing quality feedback related to the quality of the respective segmentation. For example, the feedback mechanism can allow the user to provide feedback rating the overall quality of each segmentation and/or to rate the quality of the respective segmentations with respect to accuracy, coverage, connectivity, visibility (e.g., for some lesions, sometimes they are better visible in T1 while sometimes are better visible in T2 or in CT), contour boundary/background differentiation, contrast, and the like. The feedback mechanism can also provide for receiving user feedback indicating whether artifacts are present, whether bleeding is present, and whether anatomical variants are observed. Any quality feedback received via the GUI can further be employed by the rating component 106 and/or the quality evaluation component 110.

In some embodiments, after the ranking component 106 has determined the relative rankings of the multimodal segmentations for an anatomical object, the selection component 108 can be configured to select the highest ranked segmentation modality. The selected segmentation can be presented to one or more users for clinical review (e.g., as the selected segmentation data 128), saved/stored, and/or provided to another clinical application for further usage and/or processing (e.g., depending on the intended clinical usage context for the selected segmentation).

Additionally, or alternatively, the fusion component 112 can generate a fused segmentation image for anatomical object based on the final rankings applied to each segmentation determined by the ranking component 106. With these embodiments, the fusion component 112 can projects the different segmentations of the anatomical object onto a same reference space in association with conventional image registration processes to register the respective segmentation images relative to one another and the same reference space. The fusion component 112 can further create the fused image by combining the registered segmentation images using the rankings for the contribution of each segmentation from the different modalities. In some implementations of the embodiments, the fusion component 112 can apply a weighting scheme for the different segmentation modalities based on their respective ranking scores to generate the final fused segmentation image, wherein weighted the contribution of each modality segmentation is relative to their ranking score, and wherein higher ranked segmentation modalities are given higher weight relative to lower ranked segmentation modalities. Additionally, or alternatively, the fusion component 112 can employ one or more rule-based, statistical and/or machine learning algorithms to perform the fusion of the different segmentations based at least in part on the relative rating/ranking scores. Information defining/controlling how the fusion component 112 generates the fused segmentations for anatomical objects based on the ranking scores determined for set of different multimodal segmentations can be defined by the fusion protocol data 124. For example, the fusion protocol data 124 can define rules and/or algorithms (e.g., weighted fusion algorithms, segmentation union algorithms, and the like) that can be applied by the fusion component 112 to generate a fused segmentation for an anatomical object based at least in part on the type of the anatomical object, the combination of imaging modalities in the multimodal segmentation set, and the ranking scores determined for the respective segmentations in the set. In some embodiments, the fusion protocol data 124 can include different fusion protocols or rules tailored to different anatomical objects.

Figure 3:
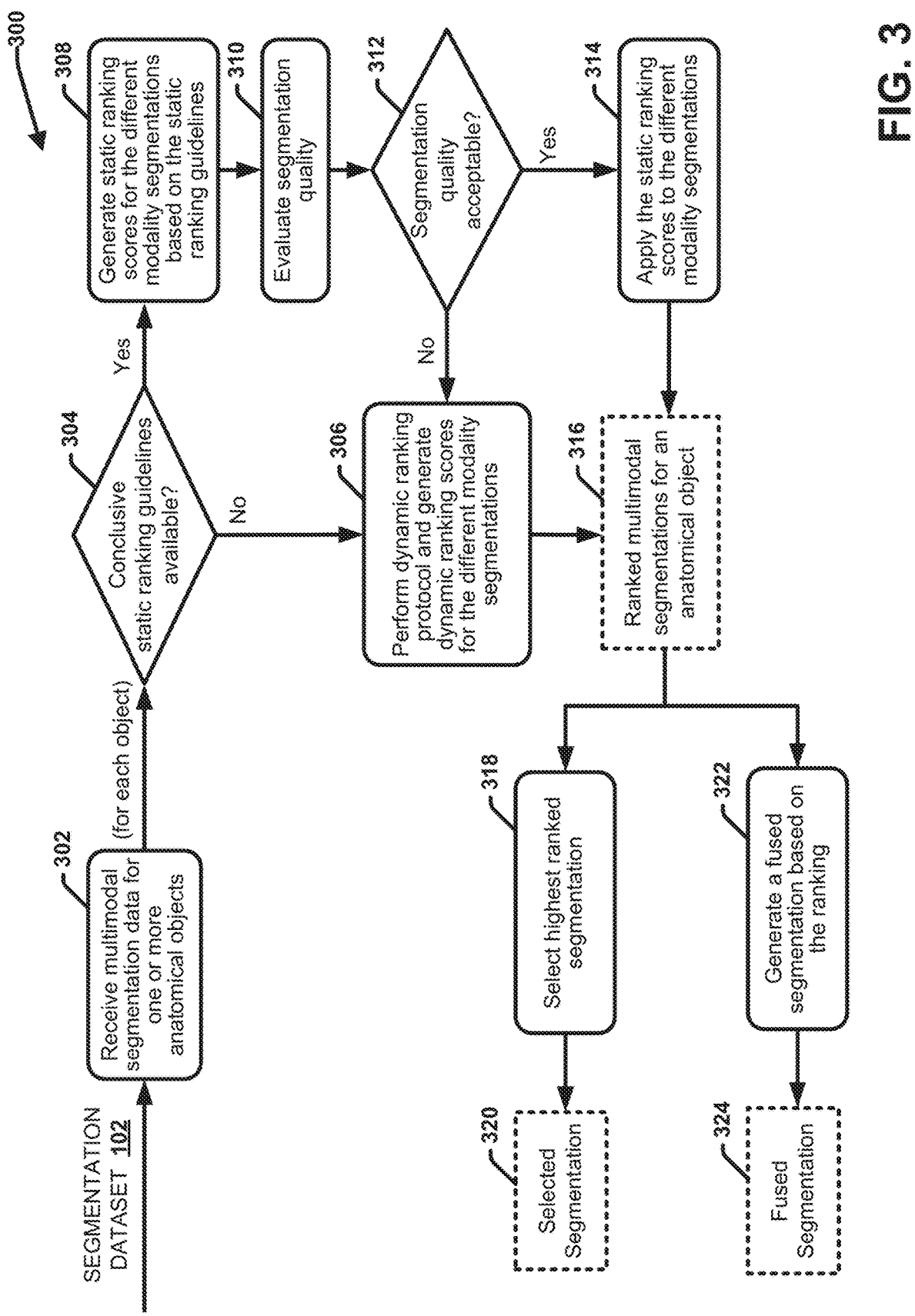
FIG. 3 presents a flow diagram of an example process for selecting and fusing multimodal segmentation data in accordance with one or more embodiments of the disclosed subject matter.

FIG. 3 presents a flow diagram of an example process 300 for selecting and fusing multimodal segmentation data in accordance with one or more embodiments of the disclosed subject matter. Process 300 corresponds to an example process that can be performed by system 100 using computing device 101 and the respective components described above. Repetitive description of like elements employed in respective embodiments is omitted for sake of brevity.

With reference to FIGS. 1 and 3, in accordance with process 300, at 302, the reception component 104 can receive the segmentation dataset 102 for one or more anatomical objects. For example, in some implementations, the segmentation dataset 102 can include a plurality of different medical images depicting the same anatomical region of a patient yet captured/generated in different modalities. Each of the different images may include multiple different organ/object segmentations (e.g., segmentation masks, segmentation image data defining the contour of the object as overlaid onto the images, etc.). In these cases, each individual organ/anatomical object segmentation should be evaluated and ranked separately. In this regard, the remainder of process 300 is described with reference to a set of multimodal segmentations (e.g., comprising two or more) for a single anatomical object.

At 304, the ranking component 106 can examine the static ranking guidelines data 120 for the anatomical object to determine whether the static ranking guidelines data provides conclusive static ranking information for the anatomical object and imaging modality combination. In this regard, conclusive ranking information refers to clear cut consensus regarding how to rank each different segmentation modality in the set for the specific anatomical object. If at 304 the ranking component 106 determines that conclusive static ranking guidelines are not available/defined for this specific anatomical object and imaging modality combination, then process 300 proceeds to 308 and the ranking component 106 proceeds with performing the dynamic ranking protocol to generate dynamic ranking scores for the different modality segmentations. In some implementations, if some static guidelines are available for the anatomical object and one or more of the imaging modalities, the ranking component 106 can factor the "partial" static ranking guidelines data for this set into the dynamic ranking determination. The result of the dynamic ranking at 306 includes ranked multimodal segmentations 316 for the anatomical object.

In accordance with process 300, if at 304 the ranking component 106 determines that conclusive static ranking guidelines are defined for the anatomical object and imaging modality combination, then process 300 proceeds to 308 and the ranking component 106 can generate or apply static ranking scores for the different modality segmentations based on the static ranking guidelines data 120.

At 310, the ranking component 106 (or the quality evaluation component 110) can further evaluate the segmentation quality of each of the different segmentations. In this regard, the ranking component 106 can check the segmentation quality based on the static ranking (noting the segmentation quality can otherwise be incorporated into the dynamic ranking protocol at 306). In one or more embodiments, the evaluation of the segmentation quality at 310 can include an evaluation of one or more quality measures associated with the respective segmentations and/or an evaluation of the one or more uncertainty measures associated with the respective segmentations (noting that the uncertainty measures are typically in agreement with the quality measures). At 312, the ranking component 106 (and/or the quality evaluation component 110) then determines whether the quality of the respective segmentations in the set is acceptable or not based on defined acceptability criterion or criteria for the one or more quality measures and/or the one or more uncertainty measures. In some implementations, the defined acceptability criterion for the quality measure and/or the uncertainty measures can vary depending on the type of the anatomical object, the type of imaging modality associated with each segmentation, and the intended clinical usage context (e.g., radiotherapy, diagnosis, disease staging, etc.). With these embodiments, information identifying or indicating the intended clinical usage context can be provided with the segmentation dataset 102, received as user feedback, and/or inferred (e.g., based at least in part on the type of the anatomical object). Information defining the acceptability criterion or criteria for the one or more quality measures and/or the one or more uncertainty measures can be included in the dynamic ranking protocol data 122.

For example, in some embodiments, at 310 the ranking component 106 can compare the corresponding segmentation model uncertainty measure (e.g., a confidence score, a DICE score, or another model certainty/uncertainty measure) associated with each segmentation in the set of multimodal segmentations to the defined acceptability criterion for the uncertainty measure, such a s a defined acceptable threshold. With these embodiments, at 312, the ranking component 106 (and/or the quality evaluation component 110) can determine that segmentation quality is not acceptable at 312 if any (e.g., one or more) of the multimodal segmentations have uncertainty measures that fail to satisfy the acceptability criterion. Process 300 can then proceed to 306 and the ranking component 106 can determine the ranking scores in accordance with the dynamic ranking protocol. Additionally, or alternatively, at 310 the ranking component 106 can compare the one or more quality measures associated with each segmentation in the set of multimodal segmentations to the defined acceptability criterion or criteria for the one or more quality measures, such a s a defined acceptable thresholds or values. With these embodiments, at 312, the ranking component 106 (and/or the quality evaluation component 110) can determine that segmentation quality is not acceptable at 312 if any (e.g., one or more) of the multimodal segmentations have one or more quality measures that fail to satisfy the quality acceptability criterion or criteria. Process 300 can then proceed to 306 and the ranking component 106 can determine the ranking scores in accordance with the dynamic ranking protocol.

In some implementations, if the ranking component 106 (or the quality evaluation component 110) determines that the segmentation quality based on the static ranking alone is acceptable, then process 300 can proceed to 314 wherein the ranking component can apply the static ranking scores to the different modality segmentations and bypass the dynamic ranking protocol. The result of the static ranking score usage at 314 also includes ranked multimodal segmentations 316 for the anatomical object.

In some embodiments, process 300 can proceed to 318, wherein the selection component selects the highest ranked segmentation from the set for clinical usage. For example, the selected segmentation 320 corresponds to the highest ranked modality segmentation from the set of multimodal segmentations included in the multimodal segmentation data for a specific anatomical object. The rendering component 116 can render or present the selected segmentation 320 to one or more users via their respective user devices 130 for clinical review and/or provide the selected segmentation 320 to another clinical application for usage thereof. Additionally, or alternatively, process 300 can proceed to 322, wherein the fusion component 112 generates a fused segmentation 324 by combining portions of the different modality segmentations based on the ranking, as discussed above. The rendering component 116 can render or present the fused segmentation to one or more users via their respective user devices 130 for clinical review and/or provide the fused segmentation to another clinical application for usage thereof.

Figure 4:
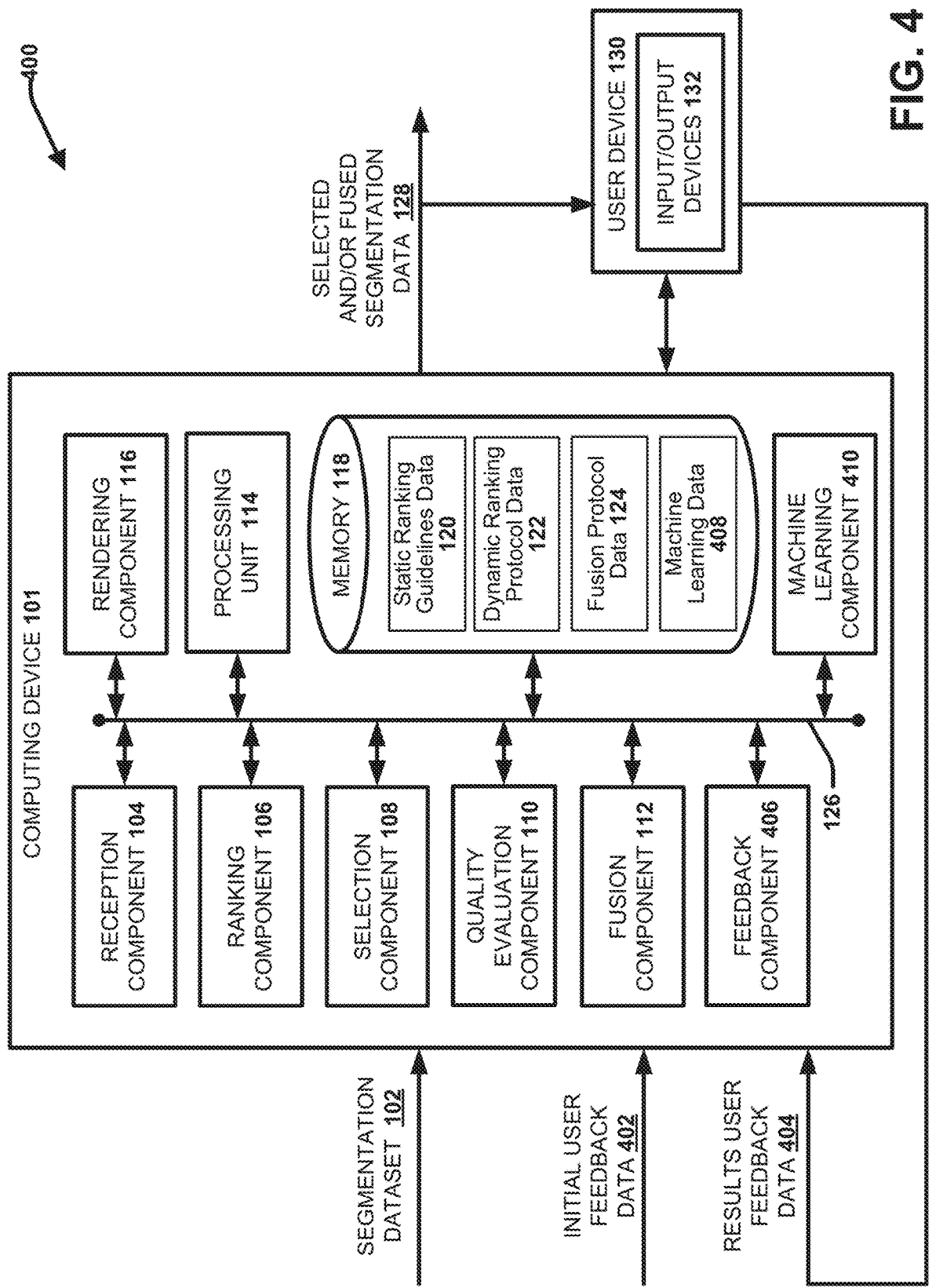
FIG. 4 illustrates another example, non-limiting system that facilitates dynamic multimodal segmentation selection and fusion in accordance with one or more embodiments of the disclosed subject matter.

FIG. 4 illustrates another example, non-limiting system 400 that facilitates dynamic multimodal segmentation selection and fusion in accordance with one or more embodiments of the disclosed subject matter. System 400 is similar to system 100 with the addition of feedback component 406, machine learning component 410 and machine learning data 408 to the computing device 101, as well as the addition of initial user feedback data 402 and results user feedback data 404. Repetitive description of like elements employed in respective embodiments is omitted for sake of brevity.

As noted above, in some embodiments, the rendering component 116 can present the segmentation dataset 102 to one or more users prior to performing the ranking to facilitate receiving user feedback (e.g., via the feedback component 406) regarding quality of the different multimodal segmentations for each anatomical object of interest segmented in the multimodal segmentation data. In the embodiment shown, this segmentation quality user feedback can be included initial user feedback data 402 provided to or otherwise received by the computing device 101. In some embodiments, the initial user feedback data 402 can additionally or alternatively include information selecting one or more specific target anatomical object included in the multimodal segmentation data for further processing (e.g., for ranking, selecting and/or fusion using the techniques described herein), in implementations in which the multimodal segmentation data includes segmentations for a plurality of different anatomical objects (e.g., such as the MR segmentation data 202 for example). The initial user feedback data 402 can also include information selecting the intended clinical usage context (e.g., radiotherapy, lesion characterization, bone metastasis analysis, diagnosis, staging, training data usage, further processing via another clinical application, etc.), which can control or influence the dynamic ranking protocol applied by the ranking component 106.

The feedback component 406 can also provide for receiving results user feedback data 404 regarding the results of the ranking component 106 and/or the fusion component 112. The results user feedback data 404 can further be aggregated over time (e.g., as machine learning data 408) and used by the machine learning component 410 in association with refining the dynamic ranking protocol data 124, refining the fusion protocol data 124, and/or to training and/or retraining corresponding machine learning models to perform the dynamic ranking and/or the segmentation fusion process (e.g., corresponding ranking/rating models 612 and/or the corresponding fusion models 712) as discussed in greater detail below. In this regard, in some embodiments, the results user feedback data 404 can include information regarding appropriateness of the rating/ranking scores applied to the different multimodal segmentations for each anatomical object by the ranking component 106. With these embodiments, in addition to the selected and/or fused segmentation data 128, the rendering component 116 can render/display (to the user at the user device 130) each of the multimodal segmentations received for an anatomical object and the corresponding ranking scores applied thereto by the ranking component 106. This feedback information can be stored in the machine learning data 408 along with the corresponding segmentations and any relevant metadata describing the features of the respective segmentations (i.e., type of anatomical object, and any of the dynamic parameters discussed herein) and used to by the machine learning component 410 to learn, define, refine and/or optimize the dynamic ranking protocol data 122 over time using one or more machine learning processes. The results user feedback data 404 can also include user feedback regarding the quality of the fused segmentation image generated by the fusion component 112. This quality feedback information can also be stored in the machine learning data 408 with the fused segmentation and the corresponding multimodal segmentations with their ranking scores (and any other information associated with the multimodal segmentations received and/or determined by the system 400) and used by the machine learning component 410 to learn, define, refine and/or optimize the fusion protocol data 124 over time using one or more machine learning processes.

Figure 5:
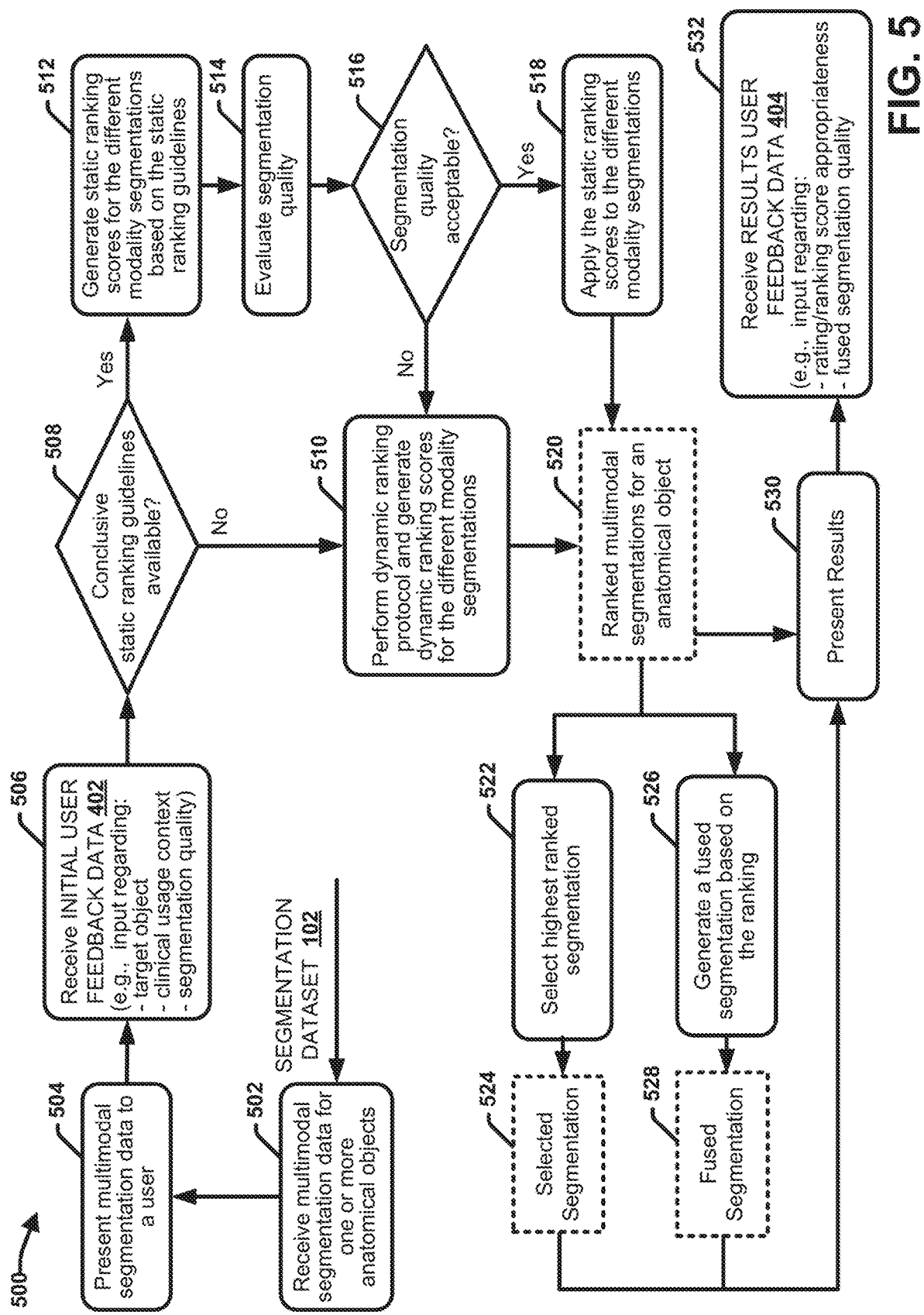
FIG. 5 presents a flow diagram of another example process for selecting and fusing multimodal segmentation data in accordance with one or more embodiments of the disclosed subject matter.

FIG. 5 presents a flow diagram of another example process 500 for selecting and fusing multimodal segmentation data in accordance with one or more embodiments of the disclosed subject matter. Process 500 corresponds to an example process that can be performed by system 400 using computing device 101 and the respective components described above. Process 500 is similar to process 300 with the additional integration of user feedback into process 500. Repetitive description of like elements employed in respective embodiments is omitted for sake of brevity.

With reference to FIGS. 4 and 5, in accordance with process 500, at 502, the reception component 104 can receive the segmentation dataset 102 for one or more anatomical objects. At 504, the rendering component can present the multimodal segmentation data to a user (e.g., a radiologist, a clinician, an engineer, a technician, etc.) in association with a request or prompt to provide the initial user feedback 402. At 506, the feedback component 406 can receive the initial user feedback data 402. As discussed above, this initial user feedback data 402 can include information selecting a specific target anatomical object included in the multimodal segmentation data for further processing (e.g., for ranking, selecting and/or fusion using the techniques described herein). The initial user feedback data 402 can also include information selecting the intended clinical usage context. The initial user feedback data 402 can also include user feedback regarding the quality of the respective segmentations associated with each of the different modalities.

At 508, for the selected target anatomical object (if selected) or otherwise for each segmentation anatomical object individual, the ranking component 106 can examine the static ranking guidelines data 120 for the selected anatomical object to determine whether the static ranking guidelines data provides conclusive static ranking information for the anatomical object and imaging modality combination. If at 504 the ranking component 106 determines that conclusive static ranking guidelines are not available/defined for this specific anatomical object and imaging modality combination, then process 500 proceeds to 510 and the ranking component 106 proceeds with performing the dynamic ranking protocol to generate dynamic ranking scores for the different modality segmentations. The result of the dynamic ranking at 510 includes ranked multimodal segmentations 520 for the anatomical object.

In accordance with process 500, if at 508 the ranking component 106 determines that conclusive static ranking guidelines are defined for the anatomical object and imaging modality combination, then process 500 proceeds to 512 and the ranking component 106 can generate or apply static ranking scores for the different modality segmentations based on the static ranking guidelines data 120. At 514, the ranking component 106 (or the quality evaluation component 110) can further evaluate the segmentation quality of each of the different segmentations as discussed above with reference to process 300. At 516, the ranking component 106 (and/or the quality evaluation component 110) then determines whether the quality of the respective segmentations in the set is acceptable or not based on the defined acceptability criterion or criteria for the one or more quality measures and/or the one or more uncertainty measures, as discussed above with reference to process 300. If at 516 the ranking component determines that the segmentation quality of the set is not acceptable, process 500 can then proceed to 510 and the ranking component 106 can determine the ranking scores in accordance with the dynamic ranking protocol. In some implementations, if at 516 the ranking component 106 (or the quality evaluation component 110) determines that the segmentation quality based on the static ranking alone is acceptable, then process 500 can proceed to 518 wherein the ranking component can apply the static ranking scores to the different modality segmentations and bypass the dynamic ranking protocol. The result of the static ranking score usage at 518 also includes ranked multimodal segmentations 520 for the anatomical object.

In some embodiments, process 500 can proceed to 518, wherein the selection component 108 selects the highest ranked segmentation from the set as the selected segmentation 524. Additionally, or alternatively, process 500 can proceed to 526, wherein the fusion component 112 generates a fused segmentation 528 by combining portions of the different modality segmentations based on the ranking, as discussed above. At 530, the rendering component can further render or present the results to the user, that is, the selected segmentation 524 and/or the fused segmentation. In some implementations, the results rendered can also include the ranked multimodal segmentations 520 for the anatomical object (e.g., with their ranking score associated therewith). In association with presenting the result at 530, the rendering component 116 can also provide the user with a prompt or request to provide the results user feedback data 404 regarding the results. At 532, the feedback component can receive the results user feedback data 404. As described above, the results user feedback data 404 can include information regarding the rating/ranking score appropriateness applied to the respective multimodal segmentations (based on review of the ranked multimodal segmentations 520) by the ranking component 106. The results user feedback data 404 can also include information regarding the quality of the fused segmentation 528. The feedback component 406 can further store the relevant input and output data along with the associated results feedback in the machine learning data 408 for usage by the machine learning component 410 in association with refining the dynamic ranking protocol data 122, refining the fusion protocol data 124, and/or to training and/or retraining corresponding machine learning models to perform the dynamic ranking and/or the segmentation fusion process (e.g., corresponding ranking/rating models 612 and/or the corresponding fusion models 712) as discussed in greater detail below.

In this regard, with reference to FIG. 4 the machine learning component 410 can employ one or more machine learning techniques to learn and define the dynamic ranking protocol data 122 based on learned patterns, correlations and/or rules between the variety of dynamic parameters discussed herein that influence the relative ranking of available multimodal segmentations for a specific anatomical object. Additionally, or alternatively, the machine learning component 410 can train and develop one or more machine learning models (e.g., referred to herein as ranking/rating models 612) to automatically infer the ranking scores for respective multimodal segmentations for a given anatomical object and clinical context based on the learned patterns, correlations and/or rules. The machine learning component 410 can similarly employ one or more machine learning techniques to learn and define the fusion protocol data 124 based on learned patterns, correlations and/or rules that influence the quality of different fused segmentation images for different anatomical objects, the segmentation protocol/rules applied to generate them, the features and rankings of the respective multimodal segmentations included in the set used to generate the fused segmentation images, and the variety of addition dynamic parameters discussed herein that influence quality of the fused segmentation image. Additionally, or alternatively, the machine learning component 410 can train and develop one or more machine learning models (e.g., referred to herein as fusion models 712) to automatically generate a fused segmentation for an anatomical object based on the respective multimodal segmentations received for the anatomical object and the learned patterns, and/or rules that influence the quality of different fused segmentation images for different anatomical objects, the segmentation protocol/rules applied to generate them, the features and rankings of the respective multimodal segmentations included in the set used to generate the fused segmentation images, and the variety of addition dynamic parameters discussed herein that influence quality of the fused segmentation image.

To facilitate this end, the machine learning component 410 can perform learning with respect to any and all of the data received by the computing device 101 (e.g., the segmentation dataset 102, the initial user feedback data 402, and the result user feedback data 404), stored by the computing device (e.g., the static ranking guidelines data 120, the dynamic ranking protocol data 122, the fusion protocol data 124 and the machine learning data 408) and generated by the computing device 101 (e.g., the ranking scores for respective multimodal segmentations and the selected and/or fused segmentation data 128). Hereinafter, any information received by the computing device 101 and generated by the computing device 101 can be aggregated over time and included in the machine learning data 408. Hereinafter, the static ranking guidelines data 120, the dynamic ranking protocol data 122, the fusion protocol data 124 and the machine learning data 408 is collectively referred to as "collective machine learning data" for the machine learning component 410.

It should be appreciated that machine learning component 410 can perform learning associated with the collective machine learning data explicitly or implicitly. Learning and/or determining inferences by the machine learning component 410 can facilitate identification and/or classification of different patterns associated with the collective machine learning data, determining one or more rules associated with collective machine learning data, and/or determining one or more relationships associated with the collective machine learning data that influence multimodal segmentation ranking and/or fusion optimization. The machine learning component 410 can also employ an automatic classification system and/or an automatic classification process to facilitate identification and/or classification of different patterns associated with the collective machine learning data, determining one or more rules associated with collective machine learning data, and/or determining one or more relationships associated with the collective machine learning data that influence multimodal segmentation ranking and/or fusion optimization. For example, the machine learning component 410 can employ a probabilistic and/or statistical-based analysis (e.g., factoring into the analysis utilities and costs) to learn one or more patterns associated with the collective machine learning data, determining one or more rules associated with collective machine learning data, and/or determining one or more relationships associated with the collective machine learning data that influence multimodal segmentation ranking and/or fusion optimization. The machine learning component 410 can employ, for example, a support vector machine (SVM) classifier to facilitate learning patterns associated with the collective machine learning data, determining one or more rules associated with collective machine learning data, and/or determining one or more relationships associated with the collective machine learning data that influence multimodal segmentation ranking and/or fusion optimization. Additionally or alternatively, the machine learning component 410 an employ other classification techniques associated with Bayesian networks, decision trees and/or probabilistic classification models. Classifiers employed by the machine learning component 410 can be explicitly trained (e.g., via a generic training data) as well as implicitly trained (e.g., via observing user behavior, receiving extrinsic information). For example, with respect to SVM's that are well understood, SVM's are configured via a learning or training phase within a classifier constructor and feature selection module. A classifier is a function that maps an input attribute vector, x=(x1, x2, x3, x4, xn), to a confidence that the input belongs to a class—that is, f(x)=confidence (class).

In an aspect, the machine learning component 410 can utilize in part inference-based schemes to facilitate learning one or more patterns associated with the collective machine learning data, determining one or more rules associated with collective machine learning data, and/or determining one or more relationships associated with the collective machine learning data that influence multimodal segmentation ranking and/or fusion optimization. The machine learning component 410 can further employ any suitable machine-learning based techniques, statistical-based techniques and/or probabilistic-based techniques. The machine learning component 410 can additionally or alternatively employ a reduced set of factors (e.g., an optimized set of factors) to facilitate generating the ranking/rating models 612 and/or the fusion models 712 discussed below. For example, the machine learning component 410 can employ expert systems, fuzzy logic, SVMs, Hidden Markov Models (HMMs), greedy search algorithms, rule-based systems, Bayesian models (e.g., Bayesian networks), neural networks, other non-linear training techniques, data fusion, utility-based analytical systems, systems employing Bayesian models, etc. In another aspect, the machine learning component 410 can perform a set of machine learning computations associated with collective machine learning data. For example, the machine learning component 410 can perform a set of clustering machine learning computations, a set of decision tree machine learning computations, a set of instance-based machine learning computations, a set of regression machine learning computations, a set of regularization machine learning computations, a set of rule learning machine learning computations, a set of Bayesian machine learning computations, a set of deep Boltzmann machine computations, a set of deep belief network computations, a set of convolution neural network computations, a set of stacked auto-encoder computations and/or a set of different machine learning computations. Any rules, patterns, and/or correlations learned by the machine learning component 410 with respect to the collective machine learning data can further be stored in the machine learning data 408, applied by the machine learning component 410 to define, and/or update/refine the dynamic ranking protocol data 122 and/or the fusion protocol data 124, and/or employed by the machine learning component 410 to train and/or retrain the ranking rating models 612 and/or the fusion models 712 discussed below.

Figure 6:
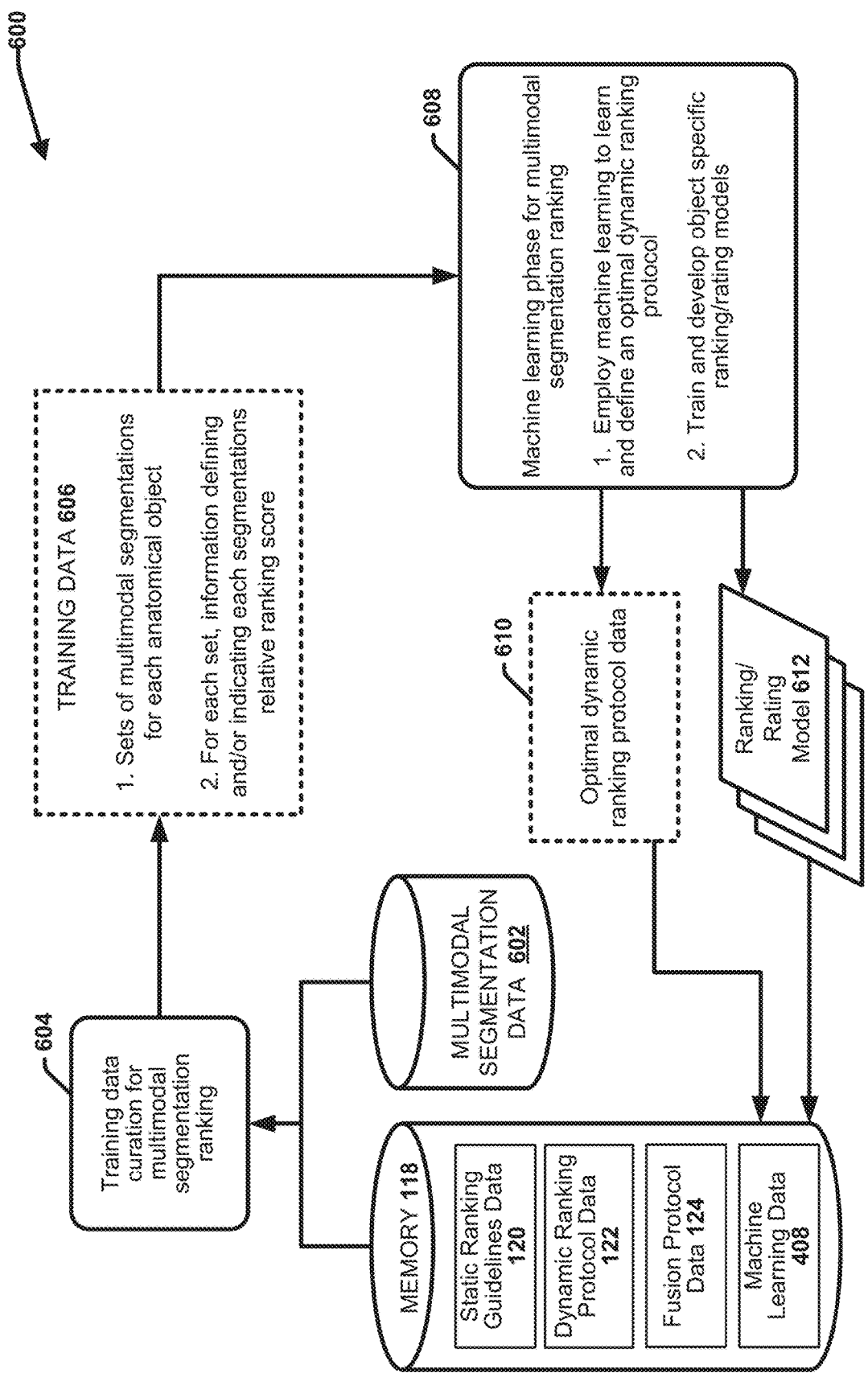
FIG. 6 presents an example machine learning framework that facilitates multimodal segmentation data ranking in accordance with one or more embodiments of the disclosed subject matter.

FIG. 6 presents an example machine learning framework 600 that facilitates multimodal segmentation data ranking in accordance with one or more embodiments of the disclosed subject matter. The machine learning framework 600 provides a high-level framework of one or more machine learning processes that can be performed by the machine learning component 410 to generate optimal dynamic ranking protocol data 610 and/or ranking/rating models 612 configured to rank or rate multimodal segmentations for one or more anatomical objects with rating or ranking scores that reflect their relative usefulness for a given clinical context.

With reference to FIGS. 5 and 6, in accordance with framework 600, at 604 the machine learning component 410 can perform training data curation for multimodal segmentation ranking. In some embodiments, this training data curation process can involve parsing through all the data available to the machine learning component 410 to identify and extract information that defines or indicates how different combinations of modality segmentations for the same anatomical object contribute to their usefulness for different clinical contexts (i.e., their relative rating score) in consideration of a variety of dynamic parameters (and parameter values) associated with the different combinations. The machine learning component 410 can perform this curation process all defined anatomical objects that may be represented in the received segmentation dataset 102 (e.g., potentially all defined anatomical objects of the human body, including all organs, all tissues, all vesicles, all types of lesions and tumors, etc.). As describe above, the training component 410 can identify and extract this information from the static ranking guidelines data 120, the dynamic ranking protocol data 122, the fusion protocol data 124 and the machine learning data 408. In this context, the machine learning data 408 can include all segmentation dataset 102 previously processed by system 100 and/or system 400 and the associated metadata, the results of the processing (e.g., the ranking scores, the fused image segmentation and potentially quality data determined by the quality evaluation component 110), and the associated initial user feedback data 404 and results user feedback data 404 (when provided). In some embodiments, at 604, the machine learning component 410 can index the extracted information for each defined anatomical object.

In one or more embodiments, as a result of the training data curation process, the machine learning component 410 can generate training data 606 that includes sets of multimodal segmentations for each anatomical object. Each of the sets can include two or more different combinations of imaging modalities. For each anatomical object, a plurality of representative sets for each possible combination of imaging modality received for the anatomical object should be included. Further, for each set, the training data 606 can include information defining and/or indicating each segmentations relative ranking score. In some implementations, this ground truth information defining the ranking scores can be provided from the previously processed segmentation dataset 102 and their previously determined ranking/rating scores (e.g., as included in the machine learning data 408). With these implementations, the sets of multimodal segmentations for each anatomical object can include the previously processed multimodal segmentation data sets. Information indicating the ranking scores can include extracted or identified features associated with each of the segmentations that correlate to its ranking score. For example, this information can include a variety of "dynamic" parameters related to segmentation quality, model uncertainty, image quality, clinical usage context, object size, object type and sub-type, imaging protocol/parameters used, imaging data source/site, image feature properties, image capture timing, image registration burdens (e.g., measure of geometrical alignment differences between the respective original images and/or the anatomical objects in the reference space), presence of bleeding, presence of artifacts, patient demography, patient pathology, and various other parameters that may be included in metadata associated with the respective multimodal segmentations described above (among others).

Additionally, or alternatively, the set of multimodal segmentations for each anatomical object can include new (unprocessed) sets of multimodal segmentation data. These new sets can be provided in and extracted from the multimodal segmentation data 602 by the machine learning component 410 in association with the training data curation process. These new sets can correspond to new instances of the segmentation dataset 102 and include or be associated with same or similar metadata described with reference thereto, including the information indicating each segmentations relative ranking score described above (e.g., the dynamic parameters).

At 608, the machine learning component 410 can perform the machine learning phase of the one or more machine learning processes. In this regard, in some embodiments, at 608, using the training data 606, the machine learning component 410 can employ one or more machine learning processes to learn and define an optimal dynamic ranking protocol (e.g., optimal dynamic ranking protocol data 610) for each anatomical object and combination of multimodal segmentation data as a function of learned correlations, patterns and/or rules between the various dynamic parameters and parameter values associated therewith. With these embodiments, the optimal dynamic ranking protocol data 610 can be used to update the dynamic ranking protocol data 122 accordingly. For example, in some implementations, machine learning component 410 can adjust the dynamic ranking protocol data 122 to reflect the optimal dynamic ranking protocol data 610. The optimal ranking protocol data 610 can further be added to memory 118.

Additionally, or alternatively, at 608, the machine learning component 410 can train and develop object specific ranking rating models 612 using the training data 606. For example, in some embodiments, the ranking/rating models 612 can include separate models tailored to different anatomical objects. The input to each model can include segmentation data for the anatomical object of any possible modality, wherein the input indicates the modality associated with each input image segmentation. In some implementations, the input can also identify the clinical context. The input can also include relevant extracted dynamic features and feature values associated with each segmentation. The output of each model can include a ranking or rating score that indicates its relative usefulness for the clinical context. With these embodiments, all multimodal segmentations in a set for an anatomical object can be processed by the same model to generate a corresponding ranking or rating score. The rating component 106 can further apply the respective scores estimated for each segmentation in a set to rank or order the segmentations accordingly.

In this regard, the ranking/rating models 612 can respectively include or correspond to machine learning models. The ranking/rating models 612 can employ various types of ML algorithms, including (but not limited to): deep learning models, neural network models, deep neural network models (DNNs), convolutional neural network models (CNNs), generative adversarial neural network models (GANs), transformers, and the like. In some implementations of these embodiments, the machine learning component 410 can employ perform a supervised machine learning process to train each model for each object using the ground truth rating information provided for the previously processed multimodal segmentations as adapted for accuracy based on the associated results user feedback (e.g., when available). The test sets can be provided by the multimodal segmentation data 602. Once trained the ranking/rating models 612 can be stored in memory 118 and applied by the ranking component 106 at runtime to newly received segmentation dataset 102 to estimate the ranking scores. With these embodiments, performance of the dynamic ranking protocol at 306 in process 300 and/or at 510 in process 500 can include application of the corresponding ranking/rating models 612 to generate the ranking scores.

Figure 7:
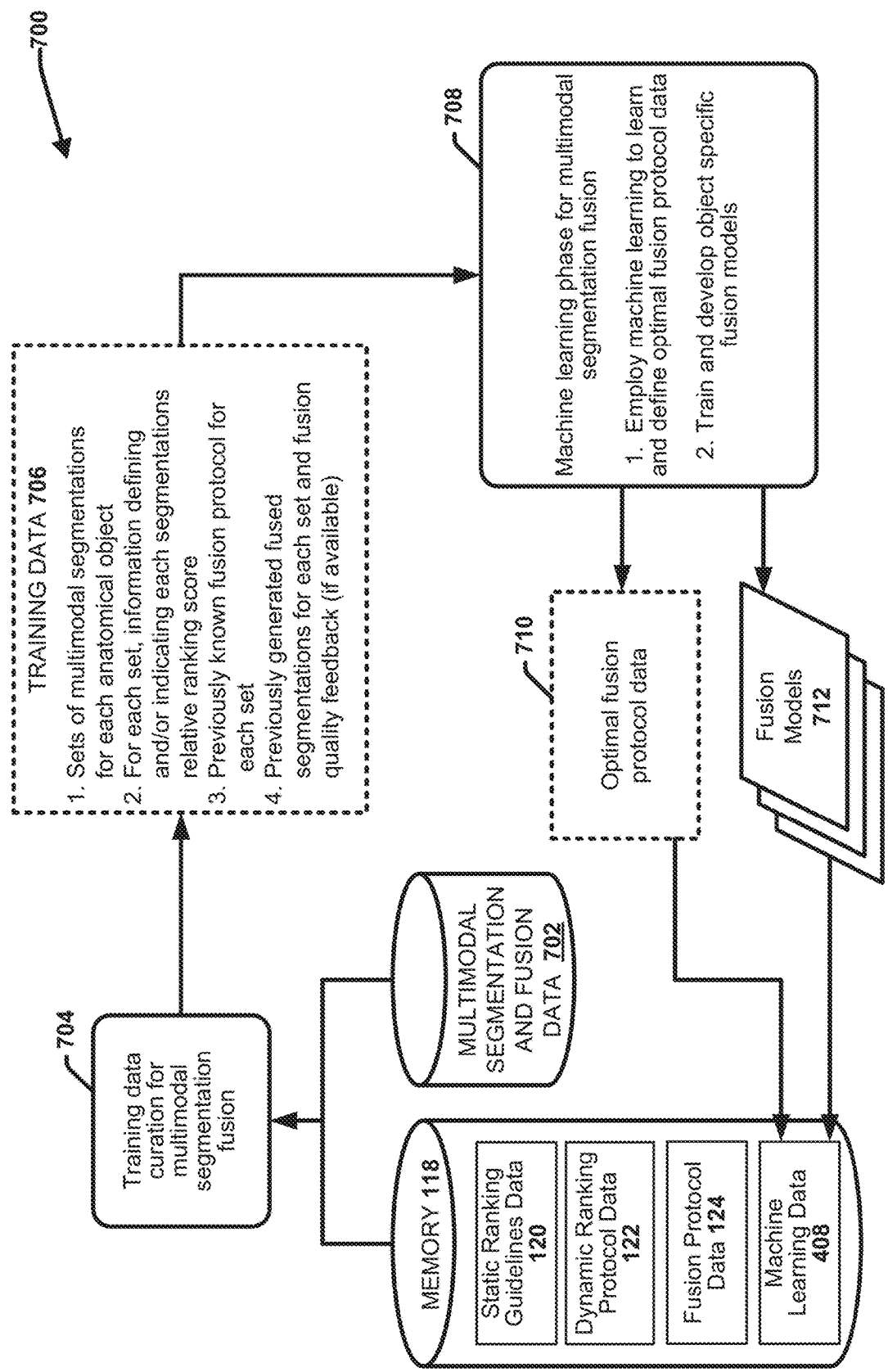
FIG. 7 presents an example machine learning framework that facilitates multimodal segmentation data fusion in accordance with one or more embodiments of the disclosed subject matter.

FIG. 7 presents an example machine learning framework 700 that facilitates multimodal segmentation data fusion in accordance with one or more embodiments of the disclosed subject matter. The machine learning framework 700 provides a high-level framework of one or more machine learning processes that can be performed by the machine learning component 410 to generate optimal fusion protocol data 710 and/or one or more fusion models 712. The optimal fusion protocol data 710 can include learned rules and/or algorithms the define how to combine different sets of multimodal segmentations for different anatomical objects into a fused segmentation image based on their respective rating/ranking scores and/or based on the different dynamic parameters/parameter values for a given clinical context. The fusion models 712 can correspond to respective machine learning models adapted to perform the same.

With reference to FIGS. 5 and 7, in accordance with framework 700, at 704 the machine learning component 410 can perform training data curation for multimodal segmentation fusion. The raining data curation at 704 can correspond to the training data curation at 604 described with reference to framework 600. Additionally, or alternatively, the training data curation process at 704 can involve more specifically identifying and extracting previously processes sets of multimodal segmentation data and the fused segmentation images generated therefore, along with the associated results user feedback evaluating the quality of the respective fused images. In some implementations, additional examples of fused segmentation images and their corresponding sets of multimodal segmentations for different anatomical objects can be provided in multimodal segmentation and fusion data 702. These additional examples can include information defining or indicating how the different multimodal segmentation were combined to generate the corresponding fused segmentations. In some implementations, the additional exemplars can be manually generated and annotated.

In one or more embodiments, as a result of the training data curation process at 704, the machine learning component 410 can generate training data 706 that includes sets of multimodal segmentations for each anatomical object. Each of the sets can include two or more different combinations of imaging modalities. For each anatomical object, a plurality of representative sets for each possible combination of imaging modality received for the anatomical object should be included. Further, for each set, the training data 606 can include information defining and/or indicating each segmentations relative ranking score, as described with reference to architecture 600. In addition, the training data 706 can include the previously known and/or applied fusion protocol for each set and previously generated fused segmentations for each set that includes fusion quality feedback (i.e., ground truth data) if available.

At 708, the machine learning component 410 can perform the machine learning phase of the one or more machine learning processes. In this regard, in some embodiments, at 708, using the training data 706, the machine learning component 410 can employ one or more machine learning processes to learn and define optimal fusion protocol data 710 for each anatomical object and combination of multimodal segmentation data as a function of learned correlations, patterns and/or rules between the various dynamic parameters and parameter values associated therewith. With these embodiments, the optimal fusion protocol data 710 can be used to update the fusion protocol data 124 accordingly. For example, in some implementations, machine learning component 410 can adjust the dynamic fusion protocol data 124 to reflect the optimal fusion protocol data 710. The optimal fusion protocol data 710 can further be added to memory 118.

Additionally, or alternatively, at 708, the machine learning component 410 can train and develop object specific fusion models 712 using the training data 706. For example, in some embodiments, the fusion models 712 can include separate models tailored to different anatomical objects. The input to each model can include the set of segmentation data for the anatomical object of including all the different imaging segmentation modalities. In this regard, the fusion models 712 can correspond to multi-channel input models, wherein the input indicates the modality associated with each input image segmentation. In some implementations, the input can also identify the clinical context. In some implementations, the input may also include the ranking or rating scores determined or estimated for each segmentation. In other implementations, the respective fusion models 712 can inherently account for this rating evaluation. The input may also include relevant extracted dynamic features and feature values associated with each segmentation. The output of each fusion model can include a fused segmentation for the input multimodal segmentation set for the anatomical object that combines the different input segmentations in an optimal fusion manner. The fusion component 112 can further apply the corresponding fusion models for the respective anatomical objects to new input multimodal segmentation sets at runtime. In this regard, performance of the fusion process at 322 in process 300 and/or at 526 in process 500 can include application of the corresponding fusion models 612 (for the specific anatomical object involved) to generate the fused segmentation. Additionally, or alternatively, the rating or ranking process can be entirely bypassed once the fusion models 612 have been trained and developed.

In this regard, the fusion models 712 can respectively include or correspond to machine learning models. The fusion models 712 can employ various types of ML algorithms, including (but not limited to): deep learning models, neural network models, DNNs, CNNs, GANs, transformers, and the like. In some implementations of these embodiments, the machine learning component 410 can employ perform a supervised machine learning process to train each fusion model 612 for each object using the previously generated fused segmentations as the ground truth exemplars. With these embodiments, only the sets with fused segmentations that are considered high quality segmentations may be used in association with training the respective fusion models to transform the input multimodal segmentations into an optimal fused segmentation image. With these embodiments, the fusion models 712 can respectively comprise transformer networks.

Figure 8:
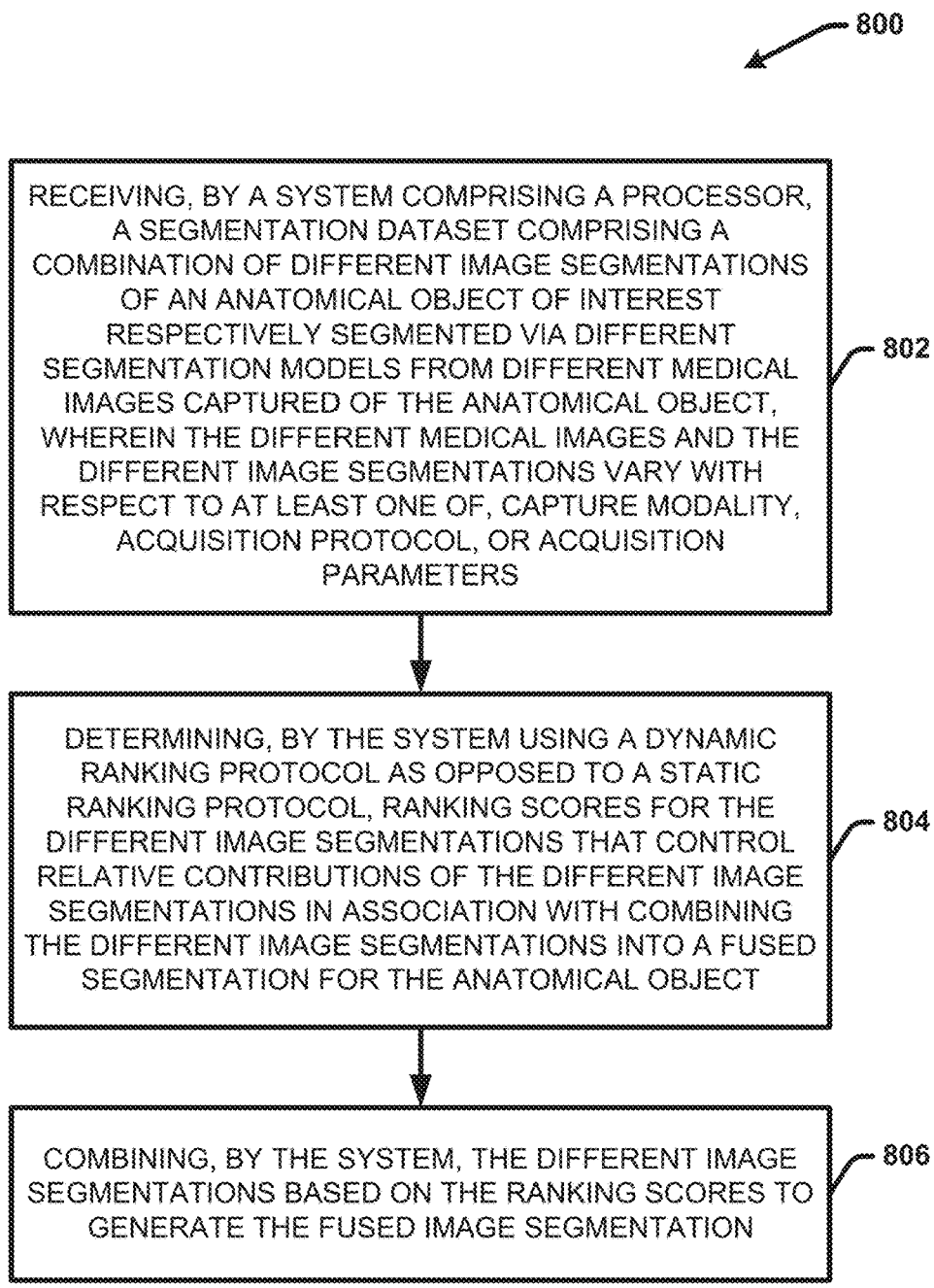
FIG. 8 illustrates a block diagram of an example, non-limiting computer implemented method for generating a fused multimodal segmentation image in accordance with one or more embodiments of the disclosed subject matter.

FIG. 8 illustrates a block diagram of an example, non-limiting computer implemented method 800 for generating a fused multimodal segmentation image in accordance with one or more embodiments of the disclosed subject matter. Repetitive description of like elements employed in respective embodiments is omitted for sake of brevity.

At 802, method 800 comprises receiving (e.g., via reception component 104), by a system comprising a processor (e.g., system 100 or system 400) a segmentation dataset (e.g., segmentation dataset 102) comprising a combination of different image segmentations of an anatomical object of interest respectively segmented via different segmentation models from different medical images captured of the anatomical object, wherein the different medical images and the different image segmentations vary with respect to at least one of, capture modality, acquisition protocol, or acquisition parameters. At 804, method 800 comprises determining, by the system, (e.g., via ranking component 106) using a dynamic ranking protocol (e.g., using dynamic ranking protocol data 122) as opposed to a static ranking protocol (e.g., using only static ranking guidelines data 120) ranking scores for the different image segmentations that control relative contributions of the different image segmentations in association with combining the different image segmentations into a fused segmentation for the anatomical object. At 806, method 800 comprises combining, by the system, (e.g., using fusion component 112) the different image segmentations based on the ranking scores to generate the fused image segmentation (e.g., fused segmentation 324, fused segmentation 528, or the like).

Figure 9:
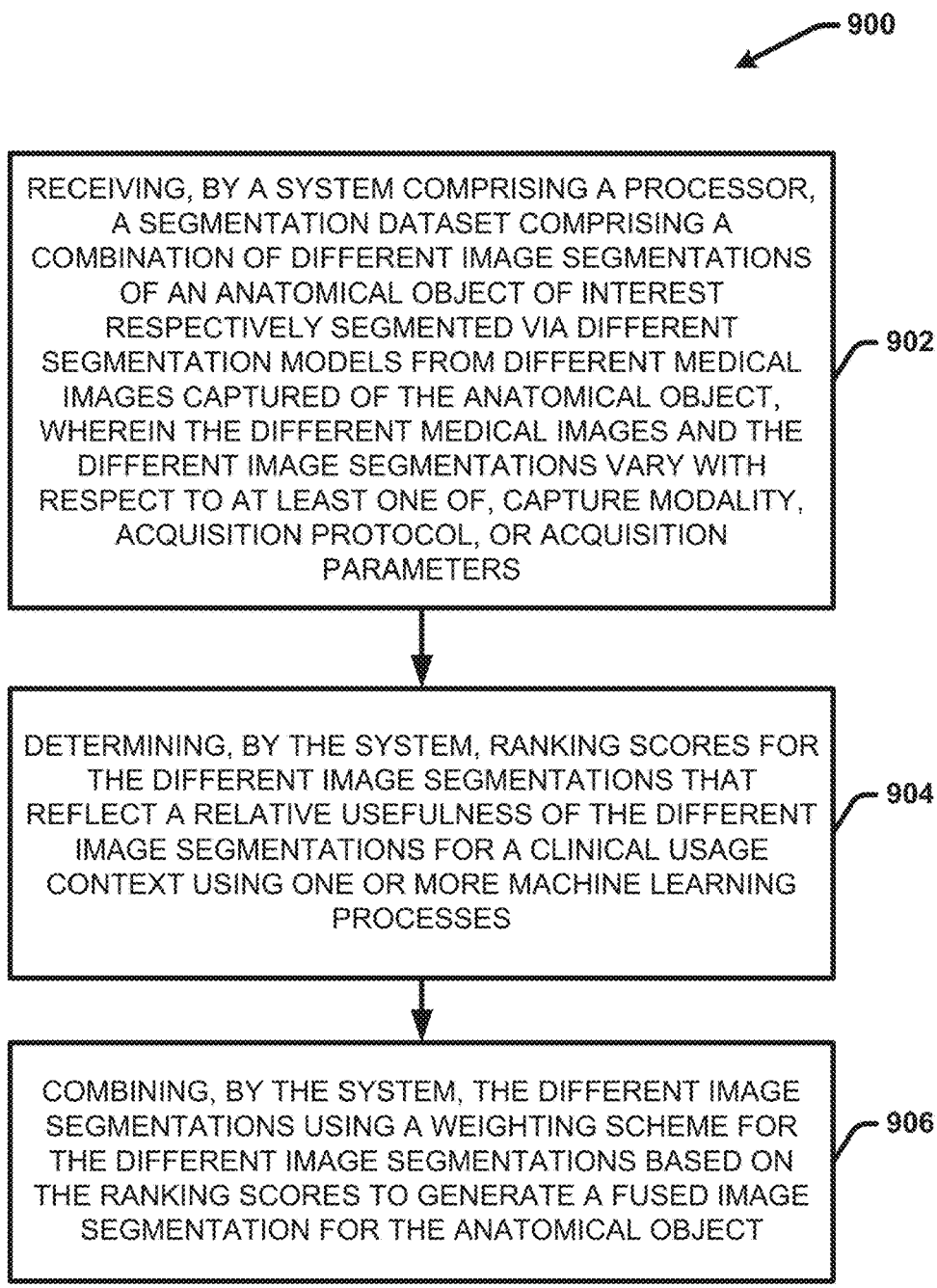
FIG. 9 illustrates a block diagram of another example, non-limiting computer implemented method for generating a fused multimodal segmentation image in accordance with one or more embodiments of the disclosed subject matter.

FIG. 9 illustrates a block diagram of another example, non-limiting computer implemented method 900 for generating a fused multimodal segmentation image in accordance with one or more embodiments of the disclosed subject matter. Repetitive description of like elements employed in respective embodiments is omitted for sake of brevity.

At 902, method 900 comprises receiving (e.g., via reception component 104), by a system comprising a processor (e.g., system 400) a segmentation dataset (e.g., segmentation dataset 102) comprising a combination of different image segmentations of an anatomical object of interest respectively segmented via different segmentation models from different medical images captured of the anatomical object, wherein the different medical images and the different image segmentations vary with respect to at least one of, capture modality, acquisition protocol, or acquisition parameters. At 904, method 900 comprises determining, by the system, (e.g., via ranking component 106 and machine learning component 410) ranking scores for the different image segmentations that reflect a relative usefulness of the different image segmentations for a clinical context using one or more machine learning processes. For example, in some embodiments, the one or more machine learning processes can include employing (e.g., by the machine learning component 110) the one or more machine learning processes to learn, define and/or update the dynamic ranking protocol data 122 that is used by the ranking component 106 to perform the ranking. Additionally, or alternatively, the one or more machine learning processes can include training, developing the ranking/rating models 612 by the machine learning component (as described with reference to machine learning framework 600) and thereafter applying (e.g., via the ranking component 106) the corresponding ranking/rating models 612 to the corresponding segmentations to generate the ranking scores. At 906, method 900 comprises combining, by the system, (e.g., using fusion component 112) the different image segmentations using a weighting scheme for the different image segmentations based on the ranking scores to generate a fused image segmentation for the anatomical object (e.g., fused segmentation 324, fused segmentation 528, or the like).

Figure 10:
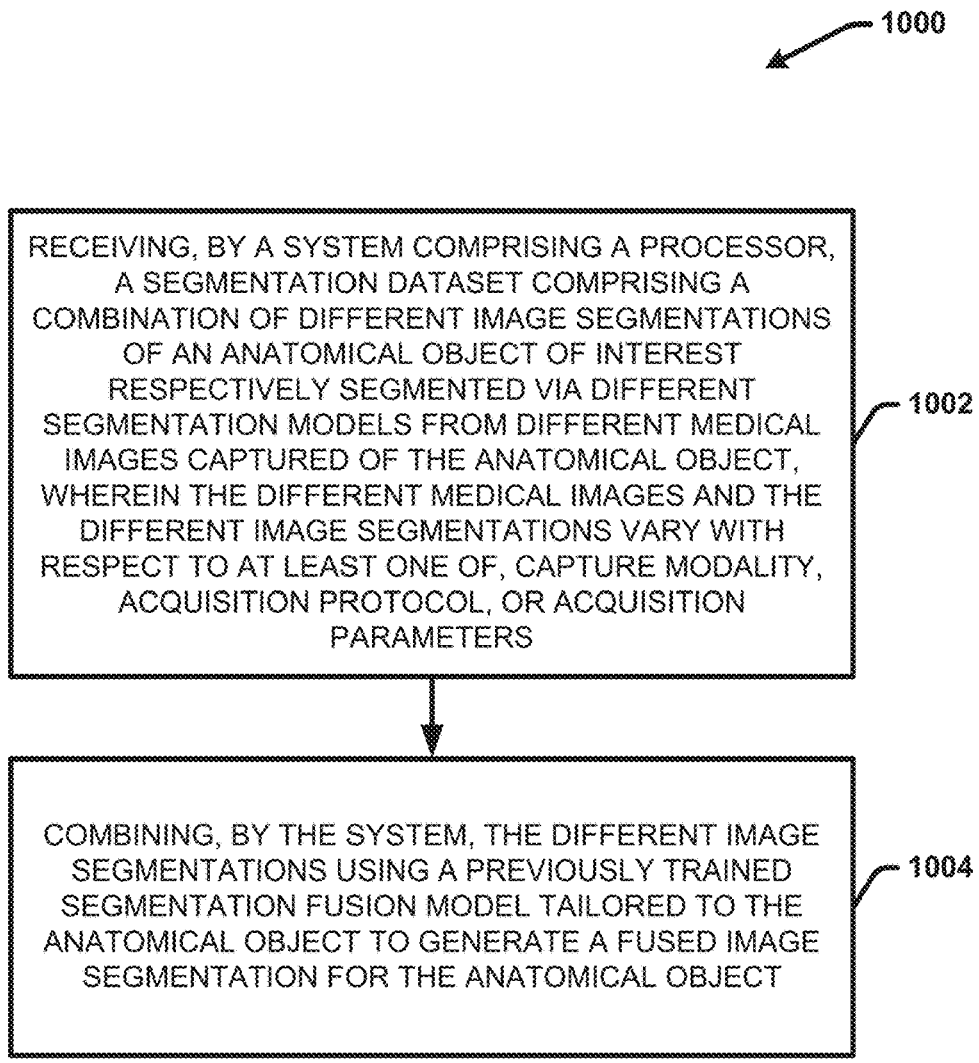
FIG. 10 illustrates a block diagram of another example, non-limiting computer implemented method for generating a fused multimodal segmentation image in accordance with one or more embodiments of the disclosed subject matter.

FIG. 10 illustrates a block diagram of another example, non-limiting computer implemented method 1000 for generating a fused multimodal segmentation image in accordance with one or more embodiments of the disclosed subject matter. Repetitive description of like elements employed in respective embodiments is omitted for sake of brevity.

At 1002, method 1000 comprises receiving (e.g., via reception component 104), by a system comprising a processor (e.g., system 400) a segmentation dataset (e.g., segmentation dataset 102) comprising a combination of different image segmentations of an anatomical object of interest respectively segmented via different segmentation models from different medical images captured of the anatomical object, wherein the different medical images and the different image segmentations vary with respect to at least one of, capture modality, acquisition protocol, or acquisition parameters. At 1004, method 1000 comprises combining, by the system (e.g., using fusion component 112) the different image segmentations using a previously trained segmentation model tailored to the anatomical object (e.g., one or more of the fusion models 712) to generate a fused image segmentation for the anatomical object (e.g., fused segmentation 324, fused segmentation 528, or the like).

One or more embodiments can be a system, a method, and/or a computer program product at any possible technical detail level of integration. The computer program product can include a computer readable storage medium (or media) having computer readable program instructions thereon for causing a processor to carry out one or more aspects of the present embodiments.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, procedural programming languages, such as the "C" programming language or similar programming languages, and machine-learning programming languages such as like CUDA, Python, Tensorflow, PyTorch, and the like. The computer readable program instructions can execute entirely on the user's computer, partly on the user's computer, as a stand-alone software package, partly on the user's computer and partly on a remote computer or entirely on the remote computer or server using suitable processing hardware. In the latter scenario, the remote computer can be connected to the user's computer through any type of network, including a local area network (LAN) or a wide area network (WAN), or the connection can be made to an external computer (for example, through the Internet using an Internet Service Provider). In various embodiments involving machine-learning programming instructions, the processing hardware can include one or more graphics processing units (GPUs), central processing units (CPUs), and the like. For example, one or more rating/ranking models 612 and/or the one or more fusion models 712 may be written in a suitable machine-learning programming language and executed via one or more GPUs, CPUs or combinations thereof. In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 11, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 11:
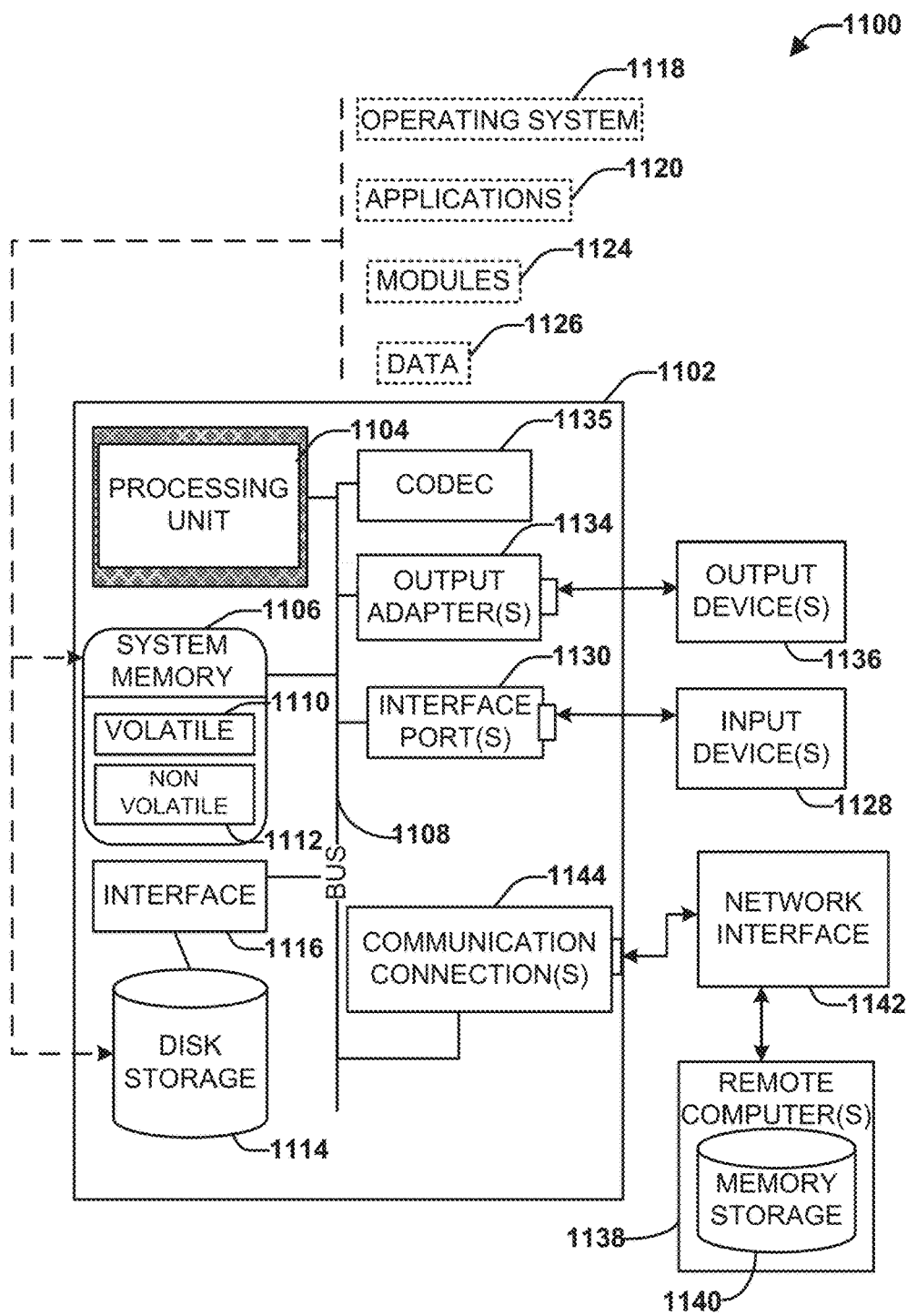
FIG. 11 illustrates a block diagram of an example, non-limiting operating environment in which one or more embodiments described herein can be facilitated.

With reference to FIG. 11, an example environment 1100 for implementing various aspects of the claimed subject matter includes a computer 1102. The computer 1102 includes a processing unit 1104, a system memory 1106, a codec 1135, and a system bus 1108. The system bus 1108 couples system components including, but not limited to, the system memory 1106 to the processing unit 1104. The processing unit 1104 can be any of various available processors. Dual microprocessors and other multiprocessor architectures also can be employed as the processing unit 1104.

The system bus 1108 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 13114), and Small Computer Systems Interface (SCSI).

The system memory 1106 includes volatile memory 1110 and non-volatile memory 1112, which can employ one or more of the disclosed memory architectures, in various embodiments. The basic input/output system (BIOS), containing the basic routines to transfer information between elements within the computer 1102, such as during start-up, is stored in non-volatile memory 1112. In addition, according to present innovations, codec 1135 can include at least one of an encoder or decoder, wherein the at least one of an encoder or decoder can consist of hardware, software, or a combination of hardware and software. Although, codec 1135 is depicted as a separate component, codec 1135 can be contained within non-volatile memory 1112. By way of illustration, and not limitation, non-volatile memory 1112 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 1112 can employ one or more of the disclosed memory devices, in at least some embodiments. Moreover, non-volatile memory 1112 can be computer memory (e.g., physically integrated with computer 1102 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 1110 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 1102 can also include removable/non-removable, volatile/non-volatile computer storage medium. FIG. 11 illustrates, for example, disk storage 1114. Disk storage 1114 includes, but is not limited to, devices like a magnetic disk drive, solid state disk (SSD), flash memory card, or memory stick. In addition, disk storage 1114 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1114 to the system bus 1108, a removable or non-removable interface is typically used, such as interface 1116. It is appreciated that disk storage 1114 can store information related to an entity. Such information might be stored at or provided to a server or to an application running on an entity device. In one embodiment, the entity can be notified (e.g., by way of output device(s) 1136) of the types of information that are stored to disk storage 1114 or transmitted to the server or application. The entity can be provided the opportunity to opt-in or opt-out of having such information collected or shared with the server or application (e.g., by way of input from input device(s) 1128).

It is to be appreciated that FIG. 11 describes software that acts as an intermediary between entities and the basic computer resources described in the suitable operating environment 1100. Such software includes an operating system 1118. Operating system 1118, which can be stored on disk storage 1114, acts to control and allocate resources of the computer system 1102. Applications 1120 take advantage of the management of resources by operating system 1118 through program modules 1124, and program data 1126, such as the boot/shutdown transaction table and the like, stored either in system memory 1106 or on disk storage 1114. It is to be appreciated that the claimed subject matter can be implemented with various operating systems or combinations of operating systems.

An entity enters commands or information into the computer 1102 through input device(s) 1128. Input devices 1128 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1104 through the system bus 1108 via interface port(s) 1130. Interface port(s) 1130 include, for example, a serial port, a parallel port, a game port, and a universal serial bus (USB). Output device(s) 1136 use some of the same type of ports as input device(s) 1128. Thus, for example, a USB port can be used to provide input to computer 1102 and to output information from computer 1102 to an output device 1136. Output adapter 1134 is provided to illustrate that there are some output devices 1136 like monitors, speakers, and printers, among other output devices 1136, which require special adapters. The output adapters 1134 include, by way of illustration and not limitation, video and sound cards that provide a means of connection between the output device 1136 and the system bus 1108. It should be noted that other devices or systems of devices provide both input and output capabilities such as remote computer(s) 1138.

Computer 1102 can operate in a networked environment using logical connections to one or more remote computers, such as remote computer(s) 1138. The remote computer(s) 1138 can be a personal computer, a server, a router, a network PC, a workstation, a microprocessor based appliance, a peer device, a smart phone, a tablet, or other network node, and typically includes many of the elements described relative to computer 1102. For purposes of brevity, only a memory storage device 1140 is illustrated with remote computer(s) 1138. Remote computer(s) 1138 is logically connected to computer 1102 through a network interface 1142 and then connected via communication connection(s) 1144. Network interface 1142 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1144 refers to the hardware/software employed to connect the network interface 1142 to the bus 1108. While communication connection 1144 is shown for illustrative clarity inside computer 1102, it can also be external to computer 1102. The hardware/software necessary for connection to the network interface 1142 includes, for exemplary purposes only, internal and external technologies such as, modems including regular telephone grade modems, cable modems and DSL modems, ISDN adapters, and wired and wireless Ethernet cards, hubs, and routers.

The illustrated aspects of the disclosure may also be practiced in distributed computing environments where certain tasks are performed by remote processing devices that are linked through a communications network. In a distributed computing environment, program modules can be located in both local and remote memory storage devices.

Figure 12:
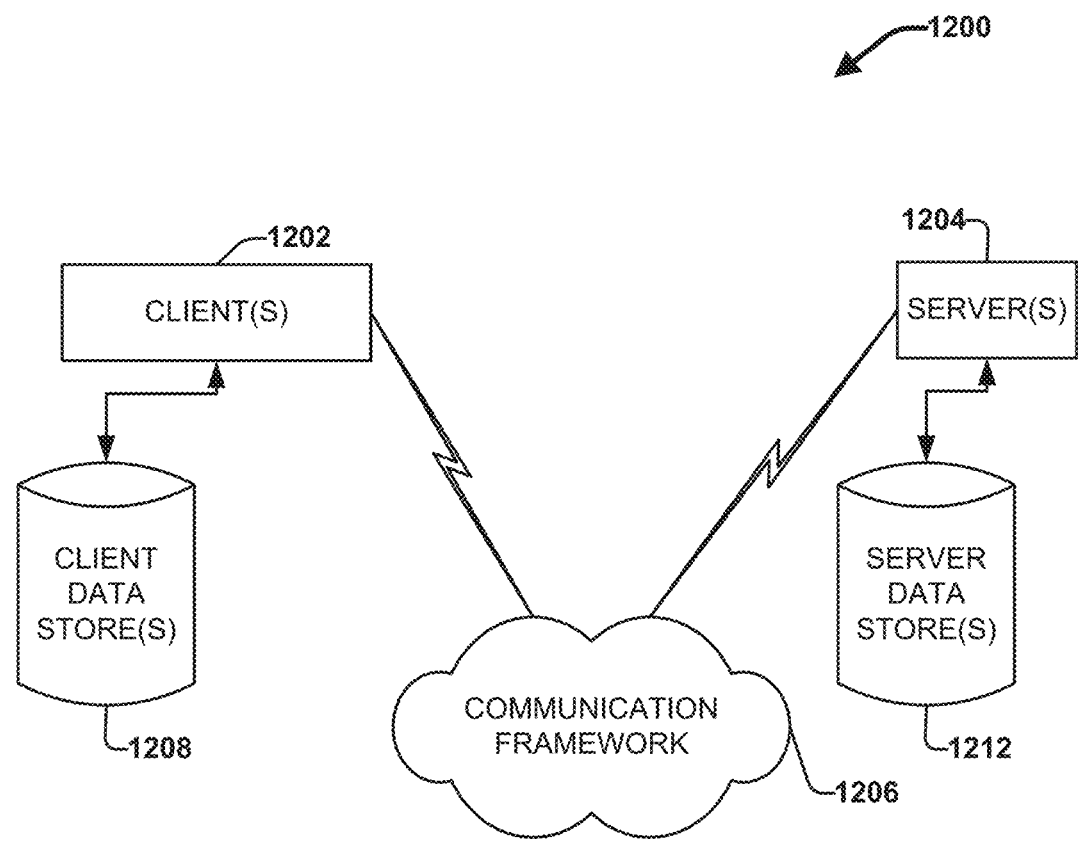
FIG. 12 illustrates a block diagram of another example, non-limiting operating environment in which one or more embodiments described herein can be facilitated.

Referring to FIG. 12, there is illustrated a schematic block diagram of a computing environment 1200 in accordance with this disclosure in which the subject systems (e.g., system 600 and the like), methods and computer readable media can be deployed. The computing environment 1200 includes one or more client(s) 1202 (e.g., laptops, smart phones, PDAs, media players, computers, portable electronic devices, tablets, and the like). The client(s) 1202 can be hardware and/or software (e.g., threads, processes, computing devices). The computing environment 1200 also includes one or more server(s) 1204. The server(s) 1204 can also be hardware or hardware in combination with software (e.g., threads, processes, computing devices). The servers 1204 can house threads to perform transformations by employing aspects of this disclosure, for example. In various embodiments, one or more components, devices, systems, or subsystems of system 400 can be deployed as hardware and/or software at a client 1202 and/or as hardware and/or software deployed at a server 1204. One possible communication between a client 1202 and a server 1204 can be in the form of a data packet transmitted between two or more computer processes wherein the data packet may include healthcare related data, training data, AI models, input data for the AI models, encrypted output data generated by the AI models, and the like. The data packet can include a metadata, e.g., associated contextual information, for example. The computing environment 1200 includes a communication framework 806 (e.g., a global communication network such as the Internet, or mobile network(s)) that can be employed to facilitate communications between the client(s) 1202 and the server(s) 1204.

Communications can be facilitated via a wired (including optical fiber) and/or wireless technology. The client(s) 122 include or are operatively connected to one or more client data store(s) 1208 that can be employed to store information local to the client(s) 1202 (e.g., the client medical image application logic 630). Similarly, the server(s) 1204 are operatively include or are operatively connected to one or more server data store(s) 812 that can be employed to store information local to the servers 1204 (e.g., the server medical image application logic 612, the segmentation model data 510, the medical image database 518, etc.)

In one embodiment, a client 1202 can transfer an encoded file, in accordance with the disclosed subject matter, to server 1204. Server 1204 can store the file, decode the file, or transmit the file to another client 1202. It is to be appreciated, that a client 1202 can also transfer uncompressed file to a server 1204 can compress the file in accordance with the disclosed subject matter. Likewise, server 1204 can encode video information and transmit the information via communication framework 1206 to one or more clients 1202.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "subsystem" "platform," "layer," "gateway," "interface," "service," "application," "device," and the like, can refer to and/or can include one or more computer-related entities or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of entity equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DR-RAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a memory that stores computer executable components; and
a processor that executes the computer executable components stored in the memory, wherein the computer executable components comprise:
a reception component that receives a segmentation dataset comprising a combination of different image segmentations of an anatomical object of interest respectively segmented via different segmentation models from different medical images captured of the anatomical object, wherein the different medical images and the different image segmentations vary with respect to capture modality;
a ranking component that employs a dynamic ranking protocol as opposed to a static ranking protocol to determine ranking scores for the different image segmentations that control relative contributions of the different image segmentations in association with combining the different image segmentations into a fused segmentation for the anatomical object, wherein the dynamic ranking protocol comprises determining the ranking scores based a plurality of parameters, comprising:
confidence measures associated with the different image segmentations that reflect measures of confidence of the different segmentation models with respect to the different image segmentations, and a type of the anatomical object; and
a fusion component that combines the different image segmentations based on the ranking scores to generate the fused image segmentation.

2. The system of claim 1, wherein the static ranking protocol comprises determining the ranking scores based solely on predefined guideline information for the combination and the type of the anatomical object, and wherein the ranking component determines the ranking scores using the dynamic ranking protocol as opposed to the static ranking protocol based on a determination that the predefined guideline information for the combination and the type of the anatomical object is unavailable or inconclusive.

3. The system of claim 1, wherein the different image segmentations are respectively associated with uncertainty measures that reflect measures of uncertainty of the one or more segmentation models with respect to the different image segmentations, and wherein the ranking component determines the ranking scores using the dynamic ranking protocol as opposed to the static ranking protocol based on a determination that one or more uncertainty measures fail to satisfy an uncertainty measure criterion.

4. The system of claim 1, wherein the ranking component determines the ranking scores using the dynamic ranking protocol as opposed to the static ranking protocol based on a determination that one or more of the different image segmentations fail to satisfy a quality criterion.

5. The system of claim 1, wherein the plurality of parameters further comprise quality measures respectively associated with the different image segmentations, wherein the quality measures are selected from the group consisting of: impact of artifacts, signal to noise ratio, and image contrast.

6. The system of claim 1, wherein the plurality of parameters further comprise a size of the anatomical object.

7. The system of claim 1, wherein the plurality of parameters further comprise acquisition protocols and acquisition parameters respectively associated with the different image segmentations.

8. The system of claim 1, wherein the dynamic ranking protocol further comprises determining the ranking scores based on predefined guideline information for the combination and the type of the anatomical object.

9. The system of claim 8, wherein the dynamic ranking protocol comprises employing one or more machine learning processes to determine the ranking scores based on the parameters and the predefined guideline information.

10. The system of claim 1, wherein the fusion component further combines the different image segmentations using a fusion protocol tailored to the combination and the type of the anatomical object.

11. The system of claim 10, wherein the fusion component employs one or more machine learning processes to learn the fusion protocol for the combination and the type based on a plurality of different manually generated fused segmentations for the combination and the type.

12. The system of claim 1, wherein the plurality of parameters further comprise: a clinical usage context for the fused image segmentation, acquisition times of the different medical images, and patient parameters of a patient from which the different medical images were captured.

13. The system of claim 1, wherein the dynamic ranking protocol comprises:
training a machine learning model to determine estimated ranking scores for respective segmentations of different combinations of different modality segmentations of the type of the anatomical object used to generate fused image segmentations for the type of the anatomical object, wherein the estimated ranking scores account for different clinical usage contexts for the fused image segmentations, uncertainty measures associated with the different modality segmentations, and quality measures associated with the different modality segmentations; and
employing a trained version of the machine learning model to determine the ranking scores for the different image segmentations of the combination based on input data identifying a clinical usage context indicated for usage of the fused image segmentation, the confidence measures, and respective quality measures associated with the different image segmentations.

14. A method, comprising:
receiving, by a system comprising a processor, a segmentation dataset comprising a combination of different image segmentations of an anatomical object of interest respectively segmented via different segmentation models from different medical images captured of the anatomical object, wherein the different medical images and the different image segmentations vary with respect to capture modality;
determining, by the system using a dynamic ranking protocol as opposed to a static ranking protocol, ranking scores for the different image segmentations that control relative contributions of the different image segmentations in association with combining the different image segmentations into a fused segmentation for the anatomical object, wherein the dynamic ranking protocol comprises determining the ranking scores based on a plurality of parameters, comprising:

confidence measures associated with the different image segmentations that reflect measures of confidence of the different segmentation models with respect to the different image segmentations, and and a type of the anatomical object; and combining, by the system, the different image segmentations based on the ranking scores to generate the fused image segmentation.

15. The method of claim 14, wherein the plurality of parameters further comprise quality measures for the different image segmentations that reflect one or more measures of quality of the different image segmentations.

16. The method of claim 15, wherein the quality measures are selected from the group consisting of: impact of artifacts, signal to noise ratio, and image contrast.

17. The method of claim 14, wherein the plurality of parameters further comprise a size of the anatomical object.

18. The method of claim 14, wherein the plurality of parameters further comprise acquisition protocols and acquisition parameters respectively associated with the different image segmentations.

19. The method of claim 18, wherein the dynamic ranking protocol comprises employing one or more machine learning processes to determine the ranking scores based on the parameters.

20. The method of claim 14, wherein the combining comprises combining the different image segmentations using a fusion protocol tailored to the combination and the type of the anatomical object.

21. The method of claim 20, further comprising:
employing, by the system, one or more machine learning processes to learn the fusion protocol for the combination and the type based on a plurality of different manually generated fused segmentations for the combination and the type.

22. A non-transitory machine-readable storage medium, comprising executable instructions that, when executed by a processor, facilitate performance of operations, comprising:
receiving a segmentation dataset comprising a combination of different image segmentations of an anatomical object of interest respectively segmented via different segmentation models from different medical images captured of the anatomical object, wherein the different medical images and the different image segmentations vary with respect to capture modality;
determining ranking scores for the different image segmentations that control relative contributions of the different image segmentations in association with combining the different image segmentations into a fused segmentation for the anatomical object, wherein the dynamic ranking protocol comprises determining the ranking scores based on a plurality of parameters, comprising:
confidence measures associated with the different image segmentations that reflect measures of confidence of the different segmentation models with respect to the different image segmentations, and and a type of the anatomical object; and
combining the different image segmentations based on the ranking scores to generate the fused image segmentation.

23. The non-transitory machine-readable storage medium of claim 22, wherein the plurality of parameters further comprise:
quality measures for the different image segmentations that reflect one or more measures of quality of the different image segmentations;
artifact information regarding presence or absence of artifacts;
acquisition protocols and acquisition parameters respectively associated with the different image segmentations; and
a size of the anatomical object.

24. The non-transitory machine-readable storage medium of claim 22, wherein the plurality of parameters further comprise: a clinical usage context for the fused image segmentation, acquisition times of the different medical images, and patient parameters of a patient from which the different medical images were captured.

25. The non-transitory machine-readable storage medium of claim 22, wherein the dynamic ranking protocol comprises:
training a machine learning model to determine estimated ranking scores for respective segmentations of different combinations of different modality segmentations of the type of the anatomical object used to generate fused image segmentations for the type of the anatomical object, wherein the estimated ranking scores account for different clinical usage contexts for the fused image segmentations, uncertainty measures associated with the different modality segmentations, and quality measures associated with the different modality segmentations; and
employing a trained version of the machine learning model to determine the ranking scores for the different image segmentations of the combination based on input data identifying a clinical usage context indicated for usage of the fused image segmentation, the confidence measures, and respective quality measures associated with the different image segmentations.

* * * * *